United States Patent
Nirogi et al.

(10) Patent No.: US 9,079,894 B2
(45) Date of Patent: Jul. 14, 2015

(54) HETEROARYL COMPOUNDS AS 5-HT$_4$ RECEPTOR LIGANDS

(75) Inventors: Ramakrishna Nirogi, Hyderabad (IN); Abdul Rasheed Mohammed, Hyderabad (IN); Suresh Yarlagadda, Hyderabad (IN); Srinivasa Rao Ravella, Hyderabad (IN); Anil Karbhari Shinde, Hyderabad (IN); Ramasastri Kambhampati, Hyderabad (IN); Praveen Kumar Roayapalley, Hyderabad (IN); Pradeep Jayarajan, Hyderabad (IN); Gopinadh Bhyrapuneni, Hyderabad (IN); Sriramachandra Murthy Patnala, Hyderabad (IN); Jyothsna Ravula, Hyderabad (IN); Venkateswarlu Jasti, Hyderabad (IN)

(73) Assignee: SUVEN LIFE SCIENCES LTD, Hyderabad (IN)

( * ) Notice: Subject to any disclaimer, the term of this patent is extended or adjusted under 35 U.S.C. 154(b) by 0 days.

(21) Appl. No.: 13/982,486

(22) PCT Filed: Jan. 5, 2012

(86) PCT No.: PCT/IN2012/000011
§ 371 (c)(1),
(2), (4) Date: Aug. 30, 2013

(87) PCT Pub. No.: WO2013/042135
PCT Pub. Date: Mar. 28, 2013

(65) Prior Publication Data
US 2014/0187581 A1   Jul. 3, 2014

(30) Foreign Application Priority Data
Sep. 19, 2011 (IN) ............................ 3203/CHE/2011

(51) Int. Cl.
| | | |
|---|---|---|
| A61K 31/445 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 211/22 | (2006.01) |
| C07D 211/32 | (2006.01) |
| C07D 413/14 | (2006.01) |
| C07D 413/06 | (2006.01) |

(52) U.S. Cl.
CPC ............ *C07D 413/14* (2013.01); *C07D 413/06* (2013.01)

(58) Field of Classification Search
None
See application file for complete search history.

(56) References Cited

U.S. PATENT DOCUMENTS

| | | | |
|---|---|---|---|
| 5,854,261 A * | 12/1998 | Bosmans | 514/320 |
| 7,943,645 B2 * | 5/2011 | Chan et al. | 514/364 |
| 2006/0194842 A1 | 8/2006 | Uchida | |
| 2008/0207690 A1 | 8/2008 | Noguchi | |
| 2008/0255113 A1 | 10/2008 | Kato | |
| 2008/0269211 A1 | 10/2008 | Ishibashi | |

FOREIGN PATENT DOCUMENTS

| | | |
|---|---|---|
| WO | WO 93/02677 A1 * | 2/1993 |
| WO | 9717345 | 5/1997 |

OTHER PUBLICATIONS

Bostrom, J. et al. Oxadiazoles in Medicinal Chemistry. Journal of Medicinal Chemistry. 2012, vol. 55, p. 1817.*
European Patent Office, "International Search Report", published under WO2013/042135 (PCT/IN2012/000011), mailed Jun. 4, 2012, and "International Preliminary Report on Patentability", mailed Sep. 5, 2013.
Berge, Stephen et al., "Pharmaceutical Salts", Journal of Pharmaceutical Sciences, 1977, pp. 1-19, vol. 66.
Ennaceur, A., Delacour, J., "A new one-trial test for neurobiological studies of memory in rats", Behav. Brain Res., 1988, pp. 47-59, vol. 31, Elsevier Science Publishers.
Humphrey, PP et al, "A Proposed New Nomenclature for 5-HT Receptors", Trends Pharmacol Sci, Jun. 1993, pp. 233-236, vol. 14, Issue 6.
Corsi, M et al, "Pharmacological analysis of 5-hydroxytryptamine effects on electrically stimulated human isolated urinary bladder", Br.J.Pharmacol, 1991, pp. 719-725, vol. 104, Issue 3.
Waikar, M.V. et al., "Evidence for an inhibitory 5-HT4 receptor in urinary bladder of rhesus and Cynomolgus monkeys", Br.J. Phamiacol, 1994, pp. 213-218, vol. 111, Issue 1.
Ford, Anthony P.D.W. et al, "The 5-HT4 Receptor", Med. Res. Rev., 1993, pp. 633-662, vol. 13, Issue 6.
Gullikson, Gary W. et al., "Gastrointestinal motility responses to the S and R enantiomers of zacopride a 5-HT4 agonist and 5-HT3 antagonist", Drug Dev. Res. 1992, pp. 405-417, vol. 26, Issue 4.

(Continued)

*Primary Examiner* — Rita Desai
*Assistant Examiner* — Ben S Michelson
(74) *Attorney, Agent, or Firm* — Iphorgan Ltd.

(57) ABSTRACT

The present invention relates to novel compounds of formula (I), and their pharmaceutically acceptable salts and compositions containing them.

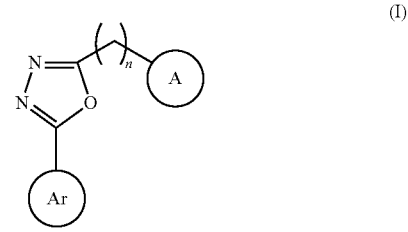

(I)

The present invention also relates to a process for the preparation of above said novel compounds, and their pharmaceutically acceptable salts. The compounds of formula (I) are useful in the treatment of various disorders that are related to 5-HT$_4$ receptors.

14 Claims, No Drawings

(56) References Cited

OTHER PUBLICATIONS

Schworer et al, "Cisplatin increases the release of 5-hydroxytryptamine (5-HT) from the isolated vascularly perfused small intestine of the guinea-pig: Involvement of 5-HT3 receptors", Naunyn-Schmiedeberg's Arch. Pharmacol, 1991, pp. 143-149, vol. 344.

Kakigami et al., "Synthesis and Structure-Activity Relationship of 3-Substituted Benzamide, Benzo[b]furan-7-carboxamide, 2,3-Dihydrobenzo[b]furan-7-carboxamide, and Indole-5-carboxamide Derivatives as Selective Serotonin 5-HT4 Receptor Agonists" Chem. Pharm. Bull., 1998, pp. 42-52, vol. 46, Issue 1.

Gaster et al., "(1-Butyl-4-piperidinyl)methyl 8-Amino-7-chloro-1,4-benzodioxane-5-carboxylate Hydrochloride: A Highly Potent and Selective 5-HT4 receptor Antagonist Derived from Metoclopramide" Journal of Medicinal Chemistry, 1993, pp. 4121-4123, vol. 36.

Brighty et al., "Synthesis of (1a,5a,6a)-6-Amino-3-azabicyclo[3.1.0]hexane, a Novel Achiral Diamine" Synlett, 1996, 1097-1099.

Kaumann et al., "A 5-HT4-like receptor in human right atrium" Naunyn-Schmiedeberg's Arch. Pharmacol, 1991, pp. 150-159, vol. 344(2).

Bostrom et al., "Oxadiazoles in Medicinal Chemistry" J. Med. Chem. 55:1817-1830 (2012).

Brown, Arthur M. And Rampe, David, "Drug-Induced Long QT Syndrome: Is HERG the Root of All Evil", Pharmaceutical News, Published 2000, pp. 15-20, vol. 7, No. 4.

Beattie, D.T., et al, "An In Vitro Investigation of the Cardiovascular Effects of the 5-HT 4 Receptor Selective Agonists, Velusetrag and TD-8954", Vascular Pharmacology (2012) pp. 1-28 doi:10.1016/j.vph.2012.11.002.

Langlois, Michel & Fischmeister, Rodolphe, "5-HT4 Receptor Ligands: Applications and New Prospects", Journal of Medicinal Chemistry, Published 2003, pp. 319-344, vol. 46, No. 3.

Letty, S., et al, "5-HT4 Receptors Improve Social Olfactory Memory in the Rat", Neuropharmacology, published 1997, pp. 681-687, vol. 36, No. 4/5.

Marchetti-Gauthier, E. et al," BIMU1 Increases Associative Memory in Rats by Activating 5-HT4 Receptors", Neuropharmacology, published 1997, pp. 697-706, vol. 36, No. 4/5.

J. Bockaert et al., "5-HT4 Receptors" Current Drug Targets—CNS & Neurological Disorders 3:39-51 (2004).

S. Consolo et al "5-HT4 receptor stimulation facilitates acetylcholine release in rat frontal cortex" NeuroReport 5:1230-1232 (1994).

C.J. Swain et al., "Novel 5-HT3 Antagonists. Indole Oxadiazoles" J. Med. Chem. 34:140-151 (1991).

* cited by examiner

HETEROARYL COMPOUNDS AS 5-HT$_4$ RECEPTOR LIGANDS

CROSS REFERENCE TO RELATED APPLICATIONS

This application is a national stage completion of PCT Application No. PCT/IN2012/000011, filed Jan. 5, 2012, and claims the benefit of Indian Application No. 3203/CHE/2011, filed Sep. 19, 2011. Each of these applications is Incorporated by reference herein.

FIELD OF INVENTION

The present invention relates to novel compounds of formula (I) and their pharmaceutically acceptable salts and compositions containing them, for treatment of various disorders that are related to 5-HT$_4$ receptors.

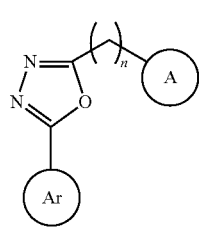

(I)

BACKGROUND OF THE INVENTION

5-HT$_4$ receptor has been officially recognized (Humphrey et al., 1993) and identified in a variety of tissues across many species (for review see Ford & Clarke, 1993). 5-HT$_4$ receptor modulators (e.g., agonists and antagonists) are found to be useful for the treatment of a variety of diseases such as gastroesophageal reflux disease, gastrointestinal disease, gastric motility disorder, non-ulcer dyspepsia, functional dyspepsia, irritable bowel syndrome, constipation, dyspepsia, esophagitis, gastroesophageral disease, nausea, central nervous system diseases, cognitive disorders, dementia, attention deficit hyperactivity disorder, schizophrenia and cardiovascular disorders such as cardiac failure and heart arryhthmia (Corsi. M et al., Pharmacological analysis of 5-hydroxytryptamine effects on electrically stimulated human isolated urinary bladder, Br. J. Pharmacol. 1991, 104(3), 719-725; Waikar. M. V et al., Evidence for an inhibitory 5-HT$_4$ receptor in urinary bladder of rhesus and Cynomolgus monkeys, Br. J. Pharmacol. 1994, 111(1), 213-218; Anthony P. D. W. Ford et al., The 5-HT$_4$ Receptor, Med. Res. Rev. 1993, 13(6), 633-662; Gary W. Gullikson et al., Gastrointestinal motility responses to the S and R enantiomers of zacopride a 5-HT$_4$ agonist and 5-HT$_3$ antagonist, Drug Dev. Res. 1992, 26(4), 405-417; Kaumann. A. J et al., A 5-HT$_4$-like receptor in human right atrium, Naunyn-Schmiedeberg's Arch. Pharmacol. 1991, 344(2), 150-159).

Patent publications US 20060194842, US 20080207690, US 20080255113 and US 20080269211 disclosed some 5-HT$_4$ receptor compounds. While some 5-HT$_4$ receptor ligands have been disclosed, and there still exists a need and scope to discover new drugs with novel chemical structures for treatment of disorders affected by 5-HT$_4$ receptor.

SUMMARY OF THE INVENTION

The present invention relates to novel 5-HT$_4$ ligand compounds of the formula (I),

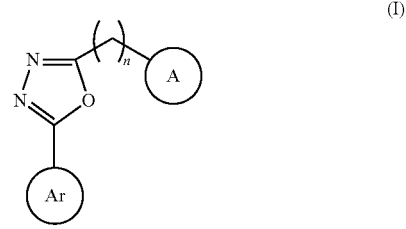

(I)

wherein,

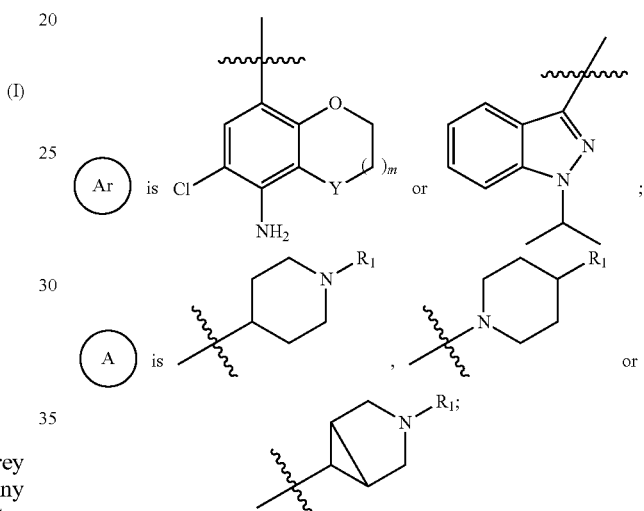

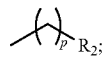 is point of attachment;

R$_1$ is alkyl, R$_3$—O—R$_3$ or

![structure](p, R2)

R$_2$ is cycloalkyl or heterocyclyl, and optionally substituted with hydrogen, alkyl or —CO—OR$_3$;
R$_3$ is alkyl;
"Y" is C or O;
"m" is an integer ranging from 0 to 1; with proviso when m is 0 then R$_1$ is cycloalkyl or heterocyclyl;
"n" is an integer ranging from 0 to 2;
"p" is an integer ranging from 0 to 1; or a pharmaceutically acceptable salt thereof.

The present invention relates to use of a therapeutically effective amount of compound of formula (I), to manufacture a medicament in the treatment of various disorders that are related to 5-HT$_4$ receptors.

Specifically, the compounds of this invention are useful in the treatment of various disorders such as attention deficit hyperactivity disorder, alzheimers disease, cognitive disorders, dementia or schizophrenia.

In another aspect, the invention relates to pharmaceutical compositions containing a therapeutically effective amount of at least one compound of formula (I), and their pharmaceutically acceptable salts thereof, in admixture with pharmaceutical acceptable excipient.

In still another aspect, the invention relates to methods for using compounds of formula (I).

In yet another aspect, the invention further relates to the process for preparing compounds of formula (I) and their pharmaceutically acceptable salts.

Representative compounds of the present invention include those specified below and their pharmaceutically acceptable salts. The present invention should not be construed to be limited to them.

6-Chloro-8-[5-(1-cyclopropyl-piperidin-4-yl)-[1,3,4]oxadiazol-2-yl]-chroman-5-ylamine hemi fumarate;
6-Chloro-8-[5-(1-cyclobutyl piperdin-4-ylmethyl)-[1,3,4]oxadiazol-2-yl]-chroman-5-yl amine L(+)-tartarate salt;
6-Chloro-8-[5-(1-cyclobutyl piperidin-4-yl methyl)-[1,3,4]oxadiazol-2-yl]-chroman-5-yl amine;
1-Isopropyl-3-{5-[1-(3-methoxy propyl)piperidin-4-yl]-[1,3,4]oxadiazol-2-yl}-1H-indazole oxalate salt;
3-[5-(1-Cyclobutyl-piperidin-4-yl methyl)-[1,3,4]oxadiazol-2-yl]-1-isopropyl-1H-indazole L(+)-tartarate salt;
6-Chloro-8-[5-(3-cyclobutyl-3-aza bicyclo[3.1.0]hex-6-yl)-[1,3,4]oxadiazol-2-yl]chroman-5-ylamine oxalate salt;
4-[5-(8-Amino-7-chloro-2,3-dihydro benzo[1,4]dioxan-5-yl)-[1,3,4]oxadiazol-2-yl]-[1,4']bipiperidinyl-1'-carboxylic acid ethyl ester oxalate salt;
5-Chloro-7-{5-[1-(tetrahydro pyran-4-yl) piperidin-4-yl]-[1,3,4]oxadiazol-2-yl}-2,3-dihydro benzofuran-4-yl amine oxalate salt;
6-Chloro-8-{5-[1-(2-methoxy-ethyl)-piperidin-4-yl]-[1,3,4]oxadiazol-2-yl}-chroman-5-ylamine;
6-Chloro-8-{5-[1-(3-methyl-butyl)-piperidin-4-yl]-[1,3,4]oxadiazol-2-yl}-chroman-5-ylamine;
6-Chloro-8-[5-(1-cyclobutylmethyl-piperidin-4-yl)-[1,3,4]oxadiazol-2-yl]-chroman-5-ylamine;
6-Chloro-8-[5-(1-cyclopropylmethyl-piperidin-4-yl)-[1,3,4]oxadiazol-2-yl]-chroman-5-ylamine;
6-Chloro-8-[5-(1-isopropyl-piperidin-4-yl)-[1,3,4]oxadiazol-2-yl]-chroman-5-ylamine;
6-Chloro-8-{5-[1-(3-methoxy-propyl)-piperidin-4-yl]-[1,3,4]oxadiazol-2-yl}-chroman-5-ylamine;
6-Chloro-8-[5-(1-cyclobutyl-piperidin-4-yl)-[1,3,4]oxadiazol-2-yl]-chroman-5-ylamine;
6-Chloro-8-[5-(1-cyclobutylmethyl-piperidin-4-yl)-[1,3,4]oxadiazol-2-yl]-2,3-dihydro-benzo[1,4]dioxin-5-ylamine;
6-Chloro-8-[5-(1-cyclobutyl-piperidin-4-yl)-[1,3,4]oxadiazol-2-yl]-2,3-dihydro-benzo[1,4]dioxin-5-ylamine;
6-Chloro-8-[5-(1-cyclopentyl-piperidin-4-yl)-[1,3,4]oxadiazol-2-yl]-chroman-5-ylamine;
6-Chloro-8-[5-(2-piperidin-1-yl-ethyl)-[1,3,4]oxadiazol-2-yl]-chroman-5-ylamine;
4-[5-(5-Amino-6-chloro-chroman-8-yl)-[1,3,4]oxadiazol-2-yl]-[1,4']bipiperidinyl-1'-carboxylic acid ethyl ester;
6-Chloro-8-[5-(3-piperidin-1-yl-propyl)-[1,3,4]oxadiazol-2-yl]-chroman-5-ylamine;
6-Chloro-8-[5-(1-cyclopentyl-piperidin-4-ylmethyl)-[1,3,4]oxadiazol-2-yl]-chroman-5-ylamine oxalate salt;
6-Chloro-8-[5-(3-isopropyl-3-aza-bicyclo[3.1.0]hex-6-yl)-[1,3,4]oxadiazol-2-yl]-chroman-5-ylamine oxalate salt;
6-Chloro-8-[5-(3-cyclobutylmethyl-3-aza-bicyclo[3.1.0]hex-6-yl)-[1,3,4]oxadiazol-2-yl]-chroman-5-ylamine oxalate salt;
6-Chloro-8-[5-(3-cyclopropylmethyl-3-aza-bicyclo[3.1.0]hex-6-yl)-[1,3,4]oxadiazol-2-yl]-chroman-5-ylamine;
6-Chloro-8-{5-[1-(tetrahydro-pyran-4-yl)-piperidin-4-yl]-[1,3,4]oxadiazol-2-yl}-chroman-5-ylamine oxalate salt;
6-Chloro-8-{5-[1-(tetrahydro-pyran-4-ylmethyl)-piperidin-4-yl]-[1,3,4]oxadiazol-2-yl}-chroman-5-ylamine oxalate salt;
5-Chloro-7-[5-(1-cyclopropyl-piperidin-4-yl)-[1,3,4]oxadiazol-2-yl]-2,3-dihydro-benzofuran-4-ylamine oxalate salt;
5-Chloro-7-[5-(1-cyclobutyl-piperidin-4-yl)-[1,3,4]oxadiazol-2-yl]-2,3-dihydro-benzofuran-4-ylamine oxalate salt;
6-Chloro-8-[5-(1-cyclopropyl-piperidin-4-yl)-[1,3,4]oxadiazol-2-yl]-2,3-dihydro-benzo[1,4]dioxin-5-ylamine oxalate salt;
6-Chloro-8-{5-[1-(tetrahydro-pyran-4-yl)-piperidin-4-yl]-[1,3,4]oxadiazol-2-yl}-2,3-dihydro-benzo[1,4]dioxin-5-ylamine oxalate salt;
6-Chloro-8-{5-[1-(3-methoxy-propyl)-piperidin-4-yl]-[1,3,4]oxadiazol-2-yl}-2,3-dihydro-benzo[1,4]dioxin-5-ylamine oxalate salt;
6-Chloro-8-{5-[1-(tetrahydro-pyran-4-ylmethyl)-piperidin-4-yl]-[1,3,4]oxadiazol-2-yl}-2,3-dihydro-benzo[1,4]dioxin-5-ylamine oxalate salt;
5-Chloro-7-{5-[1-(tetrahydro-pyran-4-ylmethyl)-piperidin-4-yl]-[1,3,4]oxadiazol-2-yl}-2,3-dihydro-benzofuran-4-ylamine oxalate;
4-[5-(4-Amino-5-chloro-2,3-dihydro-benzofuran-7-yl)-[1,3,4]oxadiazol-2-yl]-[1,4']bipiperidinyl-1'-carboxylic acid ethyl ester oxalate;
3-[5-(1-Cyclobutylmethyl-piperidin-4-yl)-[1,3,4]oxadiazol-2-yl]-1-isopropyl-1H-indazole;
1-Isopropyl-3-{5-[1-(2-methoxy-ethyl)-piperidin-4-yl]-[1,3,4]oxadiazol-2-yl}-1H-indazole;
3-[5-(1-Cyclobutyl-piperidin-4-yl)-[1,3,4]oxadiazol-2-yl]-1-isopropyl-1H-indazole;
1-Isopropyl-3-[5-(1-isopropyl-piperidin-4-yl)-[1,3,4]oxadiazol-2-yl]-1H-indazole;
3-[5-(1-Cyclopropylmethyl-piperidin-4-yl)-[1,3,4]oxadiazol-2-yl]-1-isopropyl-1H-indazole;
1-Isopropyl-3-{5-[1-(3-methyl-butyl)-piperidin-4-yl]-[1,3,4]oxadiazol-2-yl}-1H-indazole;
3-[5-(1-Cyclopropyl-piperidin-4-yl)-[1,3,4]oxadiazol-2-yl]-1-isopropyl-1H-indazole;
3-[5-(1-Cyclopentyl-piperidin-4-yl)-[1,3,4]oxadiazol-2-yl]-1-isopropyl-1H-indazole;
1-Isopropyl-3-{5-[3-(3-methoxy-propyl)-3-aza-bicyclo[3.1.0]hex-6-yl]-[1,3,4]oxadiazol-2-yl}-1H-indazole oxalate salt;
3-[5-(3-Cyclobutyl-3-aza-bicyclo[3.1.0]hex-6-yl)-[1,3,4]oxadiazol-2-yl]-1-isopropyl-1H-indazole oxalate salt;
3-[5-(3-Cyclobutylmethyl-3-aza-bicyclo[3.1.0]hex-6-yl)-[1,3,4]oxadiazol-2-yl]-1-isopropyl-1H-indazole oxalate salt;
3-[5-(3-Cyclopropylmethyl-3-aza-bicyclo[3.1.0]hex-6-yl)-[1,3,4]oxadiazol-2-yl]-1-isopropyl-1H-indazole oxalate salt;
1-Isopropyl-3-{5-[1-(tetrahydro-pyran-4-ylmethyl)-piperidin-4-yl]-[1,3,4]oxadiazol-2-yl}-1H-indazole oxalate salt;
1-Isopropyl-3-{5-[1-(tetrahydro-pyran-4-yl)-piperidin-4-yl]-[1,3,4]oxadiazol-2-yl}-1H-indazole oxalate salt;
1-Isopropyl-3-[5-(2-piperidin-1-yl-ethyl)-[1,3,4]oxadiazol-2-yl]-1H-indazole oxalate;
and
3-[5-(1-cyclobutyl piperidin-4-yl methyl)-[1,3,4]oxadiazol-2-yl]-1-isopropyl-1H-indazole oxalate salt.

DETAILED DESCRIPTION OF THE INVENTION

Unless otherwise stated, the following terms used in the specification and claims have the meanings given below:

The term "alkyl" means straight chain or branched hydrocarbon radical consisting solely of carbon and hydrogen atoms, containing no unsaturation, having from one to three carbon atoms, and which is attached to the rest of the molecule by a single bond. Exemplary "alkyl" groups include methyl, ethyl, n-propyl, iso-propyl and the like.

The term "cycloalkyl" means non-aromatic mono cyclic ring of 3 to 8 carbon atoms. Exemplary "cycloalkyl" groups include cyclopropyl, cyclobutyl, cyclopentyl and the like.

The term "heterocyclyl" means non-aromatic mono cyclic ring of 2 to 7 carbon atoms, whose ring structures include 1 to 3 heteroatoms, these additional atoms may be repeated more than once in ring. Exemplary "heterocyclyl" groups include pyrrolidinyl, piperidinyl, piperazinyl, morpholinyl and the like.

The phrase "pharmaceutically acceptable salts" indicates that the substance or composition must be compatible chemically and/or toxicologically, with the other ingredients comprising a formulation, the mammal being treated therewith.

The phrase "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

Commercial reagents were utilized without further purification. Room temperature refers to 25-40° C. Unless otherwise stated, all mass spectra were carried out using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million ($\delta$) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable excipient. The pharmaceutically acceptable excipient is carrier or diluent. Thus, the active compounds of the invention may be formulated for oral, intranasal or parenteral (e.g., intravenous, intramuscular or subcutaneous). Such pharmaceutical compositions and processes for preparing same are well known in the art (The Science and Practice of Pharmacy, D. B. Troy, 21st Edition, Williams & Wilkins, 2006).

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors.

Methods of Preparation

The compounds of formula (I) can be prepared by Scheme I & Scheme II as shown below

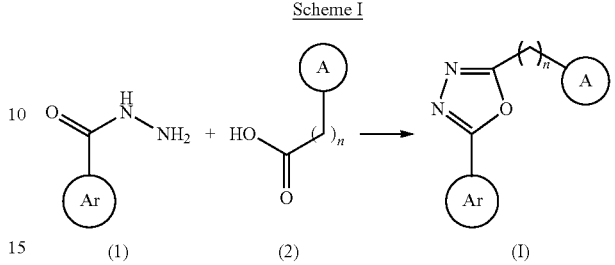

In above Scheme I, all symbols are as defined above.

The compound of formula (1) is coupled with compound of formula (2) using dehydrating agent to form compound of formula (I). The dehydrating agent is selected from group consisting of aluminium phosphate, calcium oxide, cyanuric chloride, N,N'-dicyclohexylcarbodiimide, iron(III) chloride, orthoformic acid, phosphorus pentoxide or phosphoryl chloride and more preferably selected dehydrating agent is phosphoryl chloride.

The compounds of formula (1) and formula (2) may be prepared by using preparations 1 to 9 or commercially available or can be prepared by conventional methods or by modification, using known process.

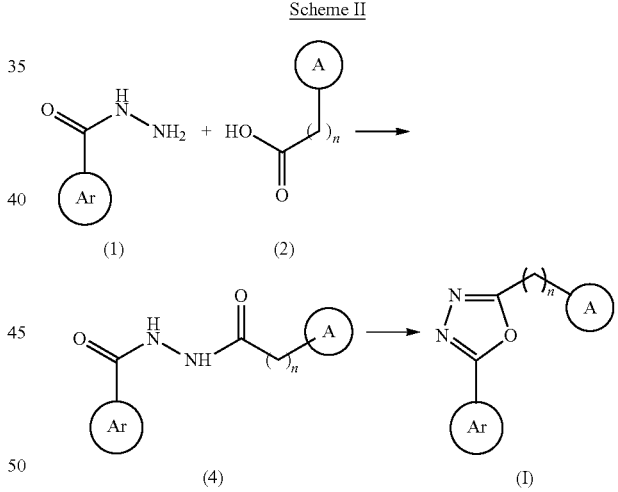

In above Scheme II, all symbols are as defined above.

The compound of formula (1) is coupled with compound of formula (2) in suitable solvent to form compound of formula (4). The compound of formula (4) is cyclized in presence of dehydrating agent to form compound of formula (I).

In the first step of the above preparation, the solvent is selected from group consisting of ethanol, tetrahydrofuran, dichloromethane, dichloroethane, toluene, dimethylformamide, dimethyl sulfoxide, 1,4-dioxan, tetrahydrofuran, triethylamine, toluene, pyridine, ethyl acetate, dichloromethane and the like or a mixture thereof and more preferably selected solvents are dichloromethane and triethylamine.

In the second step of the above preparation, the dehydrating is selected from group consisting of aluminium phosphate, calcium oxide, cyanuric chloride, N,N'-dicyclohexylcarbodiimide, iron(III) chloride, orthoformic acid, phosphorus pentoxide or phosphoryl chloride and more preferably selected dehydrating agent is phosphoryl chloride.

The compounds of formula (1) and formula (2) may be prepared by using preparations 1 to 9 or commercially available or can be prepared by conventional methods or by modification, using known process.

If necessary, pharmaceutically acceptable salts for compounds of formula (I) may be prepared conventionally by reaction with the appropriate acid or acid derivative.

Suitable pharmaceutically acceptable salts will be apparent to those skilled in the art and include those described in J. Pharm. Sci., 1977, 66, 1-19, such as acid addition salts formed with inorganic acids e. g. hydrochloric, hydrobromic, sulfuric, nitric or phosphoric acid and organic acids e.g., succinic, maleic, acetic, fumaric, citric, malic, tartaric, benzoic, p-toluic, p-toluenesulfonic, benzenesulfonic acid, methanesulfonic or naphthalenesulfonic acid. The most preferred salts of compounds of formula (I) are oxalate, tartarate, fumarate, methane sulfonate, hydrochloride and sulfate. Based on the clinical development of the compound we will select the salt form of the compound and effective dose. Oxalate salt is most preferable salt for the free base compound of Example 3 and Example 4. Fumarate salt is most preferable salt for the free base compound of Example 1. From free base compounds of Examples 1-74, the person skilled in art can easily prepare all preferred salts of this invention based on the clinical development of the compound.

EXAMPLES

The novel compounds of the present invention were prepared according to the following experimental procedures, using appropriate materials and conditions.

Preparation 1: Preparation of 5-Amino-6-chloro chroman-8-carboxylic acid hydrazide

Step (i): Preparation of Methyl 4-amino-2-hydroxy benzoate

To a stirred solution of 4-aminosalicylic acid (50 grams, 326.7 mmol) in methanol (375 mL) at 0° C. was added concentrated sulfuric acid (99.7 mL, 1.87 mmol) maintaining temperature of the reaction below 20° C. The reaction mixture was gradually heated to reflux and upon completion of the reaction after 6 hours it was cooled to ice bath temperature and basified with aqueous sodium hydroxide solution (10.0 N, 214.5 mL). The white precipitate that formed was filtered, washed with water, ether and dried under vacuum to obtain Methyl 4-amino-2-hydroxy benzoate (50.70 grams).
Yield: 93%.
$^1$H-NMR (DMSO-$d_6$): δ 10.76 (bs, 1H), 7.43 (d, J=8.6 Hz, 1H), 6.13 (bs, 2H), 6.10 (dd, J=8.6, 2.0 Hz, 1H), 5.99 (d, J=2.0 Hz, 1H), 3.79 (s, 3H); Mass (m/z): 168 (M+H)$^+$.

Step (ii): Preparation of Methyl 4-acetylamino-2-hydroxy benzoate

A solution of Methyl 4-amino-2-hydroxy benzoate (50.7 grams, 303.6 mmol, obtained in above step) in ethyl acetate (750 mL) was added to a stirred solution of water (250 mL) and sodium bicarbonate (34.9 grams, 415.5 mmol) cooled at 0° C. followed by acetyl chloride (29.7 mL, 415.5 mmol) over a period of 15 minutes. The reaction mixture was gradually warmed to room temperature and stirred for 2 hours. The two layers were separated and the organic layer was washed with brine, dried over anhydrous sodium sulphate and the solvent was removed under reduced pressure to obtain methyl 4-acetylamino-2-hydroxy benzoate (63.5 grams).
Yield: 99%.
$^1$H-NMR (CDCl$_3$): δ 10.86 (bs, 1H), 7.78 (d, J=8.6 Hz, 1H), 7.23 (s, 1H), 7.16 (bs, 1H), 7.10 (d, J=8.6 Hz, 1H), 6.13 (bs, 1H), 3.92 (s, 3H), 2.19 (s, 3H); Mass (m/z): 208 (M−H)$^+$.

Step (iii): Preparation of methyl 4-acetylamino-5-chloro-2-hydroxy benzoate To a stirred solution of methyl 4-acetylamino-2-hydroxy benzoate (61.4 grams, 294.0 mmol, obtained in above step) in dichloroethane (12 L) was added N-chlorosuccinimide (58.8 grams, 441 mmol) and the reaction mixture was refluxed for 3 hours. The volatiles were removed under reduced pressure; the solid compound thus precipitated was diluted with water (1.0 L) and filtered. The crude product was diluted with a 1:9 mixture (methanol and dichloromethane) and washed with brine. The organic layer was dried over anhydrous sodium sulphate and the volatiles were removed under reduced pressure to obtain methyl 4-acetylamino-5-chloro-2-hydroxy benzoate (67.7 grams).
Yield: 94.6%.
$^1$H-NMR (DMSO-$d_6$): δ 10.49 (bs, 1H), 9.47 (s, 1H), 7.75 (s, 1H), 7.72 (s, 1H), 3.85 (s, 3H), 2.16 (s, 3H); Mass (m/z): 244, 246 (M+H)$^+$.

Step (iv): Preparation of methyl 4-Acetylamino-5-chloro-2-(prop-2-ynyloxy)benzoate To a stirred solution of methyl 4-acetylamino-5-chloro-2-hydroxy benzoate (30 grams, 123.2 mmol, obtained in above step) in dimethylformamide (246 mL) was added potassium carbonate (42.5 grams, 308 mmol). The reaction mixture was cooled to 0° C. and propargyl bromide (22.3 mL, 150.3 mmol) was added over a period of 15 minutes. The reaction mixture was warmed to room temperature and stirred for 5 hours before being dumped in ice cold water. The solids precipitated were filtered and the crude product was dissolved in a 1:9 mixture (methanol:dichloromethane) and washed with brine solution. The organic layer was dried over anhydrous sodium sulphate and the solvent was removed under reduced pressure to obtain the title compound (25.2 grams).
Yield: 73%.
$^1$H-NMR (DMSO-$d_6$): δ 9.60 (s, 1H), 7.91 (s, 1H), 7.76 (s, 1H), 4.82 (s, 2H), 3.77 (s, 3H), 3.61 (s, 1H), 2.15 (s, 3H); Mass (m/z): 282, 284 (M+H)$^+$.

Step (v): Preparation of methyl 5-acetylamino-6-chloro-2H-chromene-8-carboxylate A stirred solution of methyl 4-acetylamino-5-chloro-2-(prop-2-ynyloxy)benzoate (25 grams, 88.8 mmol, obtained in above step) in dowtherm A (127 mL) was heated to 220° C. for 3 hours. The reaction mixture was cooled to 60-70° C. and dumped in hexane. The solids precipitated were filtered and washed with hexane to obtain methyl 5-acetylamino-6-chloro-2H-chromene-8-carboxylate (16.2 grams).
Yield: 64.8%.
$^1$H-NMR (DMSO-$d_6$): δ 9.77 (s, 1H), 7.58 (s, 1H), 6.42 (d, J=10.1 Hz, 1H), 6.04 (m, 1H), 4.83 (s, 2H), 3.78 (s, 3H), 2.06 (s, 3H);
Mass (m/z): 282, 284 (M+H)$^+$.

Step (vi): Preparation of methyl 5-acetylamino-6-chloro chroman-8-carboxylate To a solution of methyl 5-acetylamino-6-chloro-2H-chromene-8-carboxylate (20.5 grams, 72.9 mmol, obtained in above step) in ethanol (300 mL) was added Pd/C (10% w/w, 8.6 grams). The hydrogen gas pressure was applied using balloon pressure. The reaction mixture was stirred at room temperature for 5 hours and filtered through a pad of celite. The filtrate was concentrated to dryness to obtain methyl 5-acetylamino-6-chloro chroman-8-carboxylate (18.88 grams).

Yield: 91.3%.

$^1$H-NMR (DMSO-$d_6$): δ 9.65 (s, 1H), 7.55 (s, 1H), 4.16 (t, J=4.5 Hz, 2H), 3.76 (s, 3H), 2.58 (t, J=6.3 Hz, 2H), 2.05 (s, 3H), 1.87 (m, 2H); Mass (m/z): 284, 286 (M+H)$^+$.

Step (vii): Preparation of 5-Amino-6-chloro chroman-8-carboxylic acid

To methyl 5-Acetylamino-6-chloro chroman-8-carboxylate (18.88 grams, 66.6 mmol, obtained in above step), aqueous sodium hydroxide solution (1.4 N, 475 mL) was added and the reaction mixture was refluxed for 6 hours. The reaction mixture was acidified with 2N hydrochloride at 0° C. and the precipitated product was filtered and dried under vacuum to yield 5-Amino-6-chloro chroman-8-carboxylic acid (14.07 grams).

Yield: 92.9%.

$^1$H-NMR (DMSO-$d_6$): δ 11.8 (bs, 1H), 7.48 (s, 1H), 5.74 (bs, 2H), 4.09 (t, J=4.6 Hz, 2H), 2.43 (t, J=6.4 Hz, 2H), 1.91 (m, 2H); Mass (m/z): 228, 230 (M+H)$^+$.

Step (viii): Preparation of methyl 5-amino-6-chloro chroman-8-carboxylate

To a stirred solution of 5-amino-6-chloro chroman-8-carboxylic acid (13.5 grams, 59.34 mmol, obtained in above step) in methanol (68 mL) cooled at 0° C., cone sulphuric acid (18.10 mL) was added drop wise. The reaction mixture was gradually warmed to room temperature and stirred for 4 hours. The reaction mixture was cooled to 0° C., diluted with water (202 mL) and basified with sodium hydroxide (10 M, 57.9 mL). The product that precipitated was filtered and dried under vacuum to obtain methyl 5-amino-6-chloro chroman-8-carboxylate (10.5 grams).

Yield: 70.2%.

$^1$H-NMR (CDCl$_3$): δ 7.75 (s, 1H), 4.37 (bs, 2H), 4.24 (t, J=5.0 Hz, 2H), 3.83 (s, 3H), 2.49 (t, J=6.6 Hz, 2H), 2.10 (m, 2H); Mass (m/z): 242, 244 (M+H)$^+$.

Step (ix): Preparation of 5-Amino-6-chloro chroman-8-carboxylic acid hydrazide To a stirred solution of methyl 5-amino-6-chloro chroman-8-carboxylate (10.0 grams, 41.4 mmol, obtained in above step) in ethanol (82 mL), hydrazine hydrate (31.05 mL) was added. The reaction temperature was gradually increased to reflux and the reaction mixture was stirred at this temperature for 5 hours. The volatiles were removed under reduced pressure, the crude mass was dissolved in 10% methanol in dichloromethane and washed with water, brine, dried over anhydrous sodium sulphate and the solvent was removed under reduced pressure to obtain 5-Amino-6-chloro-chroman-8-carboxylic acid hydrazide (9.3 grams).

Yield: 93%.

$^1$H-NMR (DMSO-$d_6$): δ 8.85 (bs, 1H), 7.56 (s, 1H), 5.59 (bs, 2H), 4.43 (bs, 2H), 4.18 (t, J=4.8 Hz, 2H), 2.45 (t, J=6.5 Hz, 2H), 1.93 (m, 2H); Mass (m/z): 242, 244 (M+H)$^+$.

Preparation 2: Preparation of methyl 1-isopropyl-1H-indazol-3-yl carboxylate

Step (i): Preparation of methyl 1H-indazol-3-yl carboxylate

To a stirred solution of indazole-3-carboxylic acid (80.5 grams, 0.497 mmol, obtained in above step) in methanol (2 L) cooled at 0° C. was added thionyl chloride (120 mL, 1.59 mmol) over a period of 1 hour. The reaction temperature was gradually raised and the reaction mixture was refluxed for 5 hours. The volatiles were removed and the crude mass was diluted with dichloromethane, washed with aqueous sodium bicarbonate, dried over anhydrous sodium sulphate and the solvent was removed under reduced pressure to obtain the title compound (80.2 grams).

Yield: 92%.

$^1$H-NMR (CDCl$_3$): δ 13.2 (bs, 1H), 8.23 (d, J=8.2 Hz, 1H), 7.86 (d, J=8.4 Hz, 1H), 7.48 (t, J=7.4 Hz, 1H), 7.35 (t, J=7.6 Hz, 1H), 4.09 (s, 3H); Mass (m/z): 177 (M+H)$^+$.

Step (ii): Preparation of methyl 1-isopropyl-1H-indazol-3-yl carboxylate

To a stirred solution of methyl 1H-indazol-3-yl carboxylate (80.0 grams, 0.454 mmol, obtained in above step) in dry dimethylformamide (500 mL) at 0° C., sodium hydride (60% in mineral oil, 23.7 grams, 0.592 mmol) was added portion wise over a period of 30 minutes. The reaction mixture was gradually warmed to room temperature and stirred for 45 minutes before cooling it again to 0° C. To the reaction, isopropyliodide (55 mL, 0.545 mmol) was added and was stirred at room temperature for 4 hours. The reaction mixture was poured into crushed ice, stirred for 10 minutes and extracted with ethyl acetate (2×250 mL). The combined organic layer was washed with water (2×500 mL), brine, dried over anhydrous sodium sulphate and the solvent was removed under reduced pressure to get the crude mass which was purified by silica gel column to obtain methyl 1-isopropyl-1H-indazol-3-yl carboxylate (40.0 grams).

Yield: 40%.

$^1$H-NMR (CDCl$_3$): δ 8.24 (d, J=8.1 Hz, 1H), 7.52 (d, J=8.4 Hz, 1H), 7.43 (t, J=7.2 Hz, 1H), 7.31 (t, J=7.6 Hz, 1H), 4.96 (m, 1H), 4.04 (s, 3H), 1.66 (d, J=6.7 Hz, 6H); Mass (m/z): 219 (M+H)$^+$.

Step (iii): Preparation of 1-isopropyl-1H-indazol-3-yl carboxylic acid hydrazide To a stirred solution of methyl 1-isopropyl-1H-indazol-3-yl carboxylate (40.0 grams, 183.5 mmol, obtained in above step) in ethanol at room temperature hydrazine hydrate (130 mL, 2.56 mmol) was added. The reaction mixture was refluxed for 2 hours. The volatiles were removed under reduced pressure and the crude mass was diluted with dichloromethane, washed with water, brine, dried over anhydrous sodium sulphate and the solvent was removed under reduced pressure to obtain the title compound (37.52 grams).

Yield: 93%.

$^1$H-NMR (CDCl$_3$): δ 8.35 (d, J=8.1 Hz, 1H), 8.16 (bs, 1H), 7.47 (d, J=8.4 Hz, 1H), 7.41 (t, J=7.0 Hz, 1H), 7.28 (t, J=7.4 Hz, 1H), 4.87 (m, 1H), 4.09 (s, 3H), 1.60 (d, J=6.6 Hz, 6H); Mass (m/z): 219 (M+H)$^+$.

Preparation 3: Preparation of 4-Amino-5-chloro-2,3-dihydro benzofuran-7-carboxylic acid hydrazide

Step (i): Preparation of methyl 4-amino-5-chloro-2,3-dihydro benzofuran-7-carboxylate To a stirred solution of 4-amino-5-chloro-2,3-dihydro benzofuran-7-carboxylic acid (*Chem. Pharm. Bull.* 1998, 46(1), 42-52; 3.93 g, 18.4 mmol) in methanol (36.8 mL), cooled at 0° C., thionyl chloride (6.0 mL) was added. The reaction mixture was gradually warmed to room temperature and was heated to reflux for 2 hours. The volatiles were removed under reduced pressure; the crude mass was diluted with aqueous sodium bicarbonate solution and was extracted with ethyl acetate. The combined organic layer was dried over anhydrous sodium sulphate and the solvent was removed under vacuum to obtain methyl 4-amino-5-chloro-2,3-dihydro benzofuran-7-carboxylate (3.89 grams). Yield: 92.9%

$^1$H-NMR (DMSO-$d_6$): δ 7.43 (s, 1H), 6.06 (bs, 2H), 4.60 (t, J=8.8 Hz, 2H), 3.68 (s, 3H), 2.97 (t, J=8.8 Hz, 2H);

Mass (m/z): 228.0, 230.1 (M+H)$^+$.

Step (ii): Preparation of 4-amino-5-chloro-2,3-dihydro benzofuran-7-carboxylic acid hydrazide To a stirred solution of methyl 4-amino-5-chloro-2,3-dihydro benzofuran-7-carboxylate (3.88 grams, 17.07 mmol, obtained in the above step) in ethanol (34.1 mL), hydrazine hydrate (11.5 mL, 236.2) was added. The reaction temperature was gradually increased to reflux and the reaction mixture was stirred at this temperature for 5 hours. The volatiles were removed under reduced pressure, the crude mass was triturated with plenty of ether and pentane to obtain 4-Amino-5-chloro-2,3-dihydro benzofuran-7-carboxylic acid hydrazide (3.76 grams).

Yield: 96%.

$^1$H-NMR (DMSO-$d_6$): δ 8.35 (bs, 1H), 7.44 (s, 1H), 5.85 (s, 2H), 4.68 (t, J=8.7 Hz, 2H), 4.43 (bs, 2H), 3.0 (t, J=8.7 Hz, 2H);

Mass (m/z): 228.0, 230.1 (M+H)$^+$.

Preparation 4: Preparation of 8-Amino-7-chloro-2,3-dihydro benzo[1,4]dioxane-5-carboxylic acid hydrazide

Step (i): Preparation of methyl 8-amino-7-chloro-2,3-dihydro benzo[1,4]dioxane-5-carboxylate To a stirred solution of 8-Amino-7-chloro-2,3-dihydro-benzo[1,4]dioxine-5-carboxylic acid (*Journal of Medicinal Chemistry*, 1993, 36, 4121; 2.2 grams, 9.58 mmol) in methanol (38.3 mL), cooled at 0° C. thionyl chloride (2.78 mL) was added. The reaction mixture was gradually warmed to room temperature and then heated to reflux for 3 hours. The volatiles were removed under reduced pressure; the crude mass was diluted with aq. sodium bicarbonate solution and extracted with ethyl acetate. The combined organic layer was dried over anhydrous sodium sulphate and the solvent was removed under vacuum to obtain the title compound (2.12 grams).

Yield: 90.9%

$^1$H-NMR (CDCl$_3$): δ 7.52 (s, 1H), 4.47 (bs, 2H), 4.45-4.30 (m, 4H), 3.84 (s, 3H). Mass (m/z): 244.1, 246.1 (M+H)$^+$.

Step (ii): Preparation of 8-Amino-7-chloro-2,3-di hydro benzo[1,4]dioxane-5-carboxylic acid hydrazide To a stirred solution of methyl 8-amino-7-chloro-2,3-dihydro-benzo[1,4]dioxine-5-carboxylate (2.1 grams, 8.6 mmol, obtained in the above step) in ethanol (34.4 mL), hydrazine hydrate (6.2 mL, 129.3 mmol) was added. The reaction temperature was gradually increased to reflux and the reaction mixture was stirred at this temperature for 5 hours. The volatiles were removed under reduced pressure, the crude mass was triturated with plenty of ether and pentane to obtain 8-amino-7-chloro-2,3-dihydro benzo[1,4]dioxane-5-carboxylic acid hydrazide (2.1 grams).

Yield: 100%.

$^1$H-NMR (DMSO-$d_6$): δ 8.80 (bs, 1H), 7.27 (s, 1H), 5.40 (bs, 2H), 4.46 (bs, 2H), 4.40-4.25 (m, 4H); Mass (m/z): 244.1, 246.1 (M+H)$^+$.

Preparation 5: Preparation of 1-cyclopropyl piperidine-4-carbonyl chloride

Step (i): Preparation of 1-cyclopropyl piperidine-4-carbonitrile

To a stirred solution of 1-cyclopropyl-4-piperidone (Alfa Aesar, 3.0 grams, 21.5 mmol) in a mixture of 1,2-dimethoxyethane (72 mL) and ethanol (2.2 mL) cooled at 0° C., was added p-toluenesulfonylmethylisocyanide (5.45 grams, 27.95 mmol). Solid potassium tertiary butoxide (5.54 grams, 49.45 mmol) was added over a period of 1 hour. The reaction mixture was stirred at this temperature for additional 1 hour and gradually warmed to room temperature. After stirring for 2 hours at this temperature, it was cooled to 0° C., diluted with brine and ethyl acetate. The organic layer was separated, dried over anhydrous sodium sulphate and the solvent was removed under reduced pressure to obtain crude product, which was purified by slica gel column to yield 1-cyclopropyl piperidine-4-carbonitrile (1.32 grams).

Yield: 41.2%.

$^1$H-NMR (CDCl$_3$): δ 2.82 (m, 2H), 2.63 (m, 1H), 2.49 (m, 2H), 1.98-1.78 (m, 4H), 1.70-1.58 (m, 1H), 0.50-0.40 (m, 2H), 0.40-0.35 (m, 2H); Mass (m/z): 151 (M+H)$^+$.

Step (ii): Preparation of 1-cyclopropyl piperidine-4-carboxylic acid

A mixture of 1-cyclopropyl piperidine-4-carbonitrile (1.32 grams, 8.8 mmol, obtained in the above step) and hydrochloric acid (6 N, 35.2 mL) was refluxed for 3 hours. The volatiles were removed under reduced pressure; the traces of water were removed by co distilling with toluene. The crude product thus obtained was triturated with ether several times and dried under vacuum to obtained 1-cyclopropyl piperidine-4-carboxylic acid (2.02 grams).

Yield: 100%.

$^1$H-NMR (DMSO-$d_6$): δ 12.54 (bs, 1H), 10.79 (bs, 1H), 3.50-3.40 (m, 2H), 3.18-3.0 (m, 2H), 2.78-2.65 (m, 1H), 3.55-3.45 (m, 1H), 2.10-1.85 (tn, 4H), 1.20-1.10 (m, 2H), 0.80-0.70 (m, 2H);
Mass (m/z): 170 (M+H)⁺.

Step (iii): Preparation of 1-cyclopropyl piperidine-4-carbonyl chloride

To a stirred mixture of 1-cyclopropyl piperidine-4-carboxylic acid (10.0 grams, 48.6 mmol, obtained in above step) in dichloromethane (198 mL) cooled at 0° C. was added dry dimethyl formamide (2 mL) followed by drop wise addition of oxalyl chloride (12.5 mL, 145.8 mmol). The reaction mixture was gradually warmed to room temperature and stirred for 1 hour. The volatiles were removed under reduced pressure and the crude 1-cyclopropyl piperidine-4-carbonyl chloride (11.0 grams). This crude product was used in the next reaction without purification.
Yield: 100%.
¹H-NMR (DMSO-$d_6$): δ 10.66 (bs, 1H), 3.50-3.42 (m, 2H), 3.40-3.30 (m, 1H), 3.15-3.0 (m, 2H), 2.80-2.65 (m, 1H), 2.10-1.80 (m, 4H), 1.15-1.08 (m, 2H), 0.80-0.70 (m, 2H);
Mass (m/z): 184 (M+H)⁺.

Preparation 6: Preparation of (1-cyclobutyl piperidin-4-yl) acetic acid

Step (i): Preparation of t-butyl 4-ethoxycarbonylmethylene piperidine-1-carboxylate To a stirred solution of 1-Boc-4-piperidone (2.0 grams, 10.03 mmol) in benzene (40 mL) at room temperature was added Wittig reagent (5.23 grams, 15 mmol). The reaction mixture was refluxed for 10 hours and the volatiles were removed under reduced pressure to obtain a crude mass which was purified by silica gel column chromatography to obtain t-butyl 4-ethoxycarbonylmethylene piperidine-1-carboxylate (2.05 grams).
Yield: 76%.
¹H-NMR (CDCl₃): δ 5.71 (s, 1H), 4.16 (q, 2H), 3.55-3.45 (m, 4H), 2.94 (t, J=5.7 Hz, 2H), 2.28 (t, J=5.6 Hz, 2H), 1.47 (s, 9H), 1.28 (t, J=7.1 Hz, 3H); Mass (m/z): 270 (M+H)⁺.

Step (ii): Preparation of t-butyl 4-ethoxycarbonylmethyl piperidine-1-carboxylate To a stirred solution of t-butyl 4-ethoxycarbonylmethylene piperidine-1-carboxylate (2.05 grams, 7.62 mmol, obtained in above step) in ethanol (30 mL) at room temperature was added Pd/C (10 wt %, 600 mg). Hydrogen balloon pressure was applied on the reaction for 5 hours. The reaction mixture was filtered through a pad of celite and the volatiles were removed under reduced pressure to obtain t-butyl-4-ethoxycarbonylmethyl piperidine-1-carboxylate (1.98 grams).
Yield: 95.8%.
¹H-NMR (CDCl₃): δ 4.20-4.0 (m, 4H), 2.83-2.65 (m, 2H), 2.23 (d, J=6.8 Hz, 2H), 2.0-1.88 (m, 1H), 1.75-1.68 (m, 2H), 1.45 (s, 9H), 1.26 (t, J=7.0 Hz, 3H), 1.25-1.05 (m, 2H);
Mass (m/z): 272 (M+H)⁺.

Step (iii): Preparation of piperidin-4-yl acetic acid ethyl ester

To a stirred solution of t-butyl 4-ethoxycarbonylmethyl piperidine-1-carboxylate (1.98 grams, 7.3 mmol, obtained in the above step) in isopropyl alcohol (5 mL) cooled at 0° C., was added a solution of dry isopropanolic hydrogen chloride (~3 N, 15 mL). The reaction mixture was stirred at room temperature for 16 hours. The volatiles were removed under reduced pressure and the crude product was triturated with ether several times, dried under vacuum to obtain piperidin-4-yl acetic acid ethyl ester (1.57 grams)
Yield: 100%.
¹H-NMR (DMSO-$d_6$): δ 4.03 (q, 2H), 3.23-3.15 (m, 2H), 2.86-2.78 (m, 2H), 2.24 (d, J=6.8 Hz, 2H), 2.0-1.85 (m, 1H), 1.81-1.72 (m, 2H), 1.40-1.25 (m, 2H), 1.14 (t, J=6.9 Hz, 3H);
Mass (m/z): 172 (M+H)⁺.

Step (iv): Preparation of (1-cyclobutyl piperidin-4-yl) acetic acid ethyl ester A mixture of cyclobutanone (0.3 mL, 3.94 mmol) in acetic acid (0.19 mL, 3.28 mmol) was added to a stirred solution of piperidin-4-yl acetic acid ethyl ester (562 mg, 3.28 mmol, obtained in above step) in dichloromethane cooled at 0° C. Solid sodium triacetoxyborohydride (1.39 grams, 7.2 mmol) was added portion wise over a period of 15 minutes. The reaction mixture was gradually warmed to room temperature and stirred for 16 hours. The reaction mixture was cooled to 0° C. and basified with saturated sodium bicarbonate solution (pH: 7.5). The two layers were separated, the organic layer was washed with brine, dried over anhydrous sodium sulphate and the volatiles were removed under reduced pressure to obtain (1-Cyclobutyl piperidin-4-yl) acetic acid ethyl ester (652 mg).
Yield: 88.3%.
¹H-NMR (CDCl₃): δ 4.13 (q, 2H), 2.90-2.82 (m, 2H), 2.75-2.62 (m, 1H), 2.22 (d, J=6.9 Hz, 2H), 2.10-1.95 (m, 2H), 1.95-1.80 (m, 2H), 1.80-1.60 (m, 7H), 1.35-1.20 (m, 2H), 1.27 (t, J=7.1 Hz, 3H); Mass (m/z): 226 (M+H)⁺.

Step (v): Preparation of (1-cyclobutyl piperidin-4-yl) acetic acid

To a stirred mixture of (1-cyclobutyl piperidin-4-yl) acetic acid ethyl ester (652.9 mg, 2.90 mmol, obtained in above step), tetrahydrofuran (6 mL) and water (6.0 mL) cooled at 0° C. lithium hydroxide monohydrate (133 mg, 3.19 mmol) was added in a single lot. The reaction mixture was stirred at room temperature for 16 hours. The reaction mixture was cooled again to 0° C. and acidified with 2N hydrochloric acid to pH: 2-3. The volatiles were removed under reduced pressure and the traces of water were removed by azeotropic distillation with toluene to obtain (1-cyclobutyl piperidin-4-yl) acetic acid (747.9 mg).
Yield: 100%.
¹H-NMR (DMSO-$d_6$): δ 12.25 (bs, 1H), 10.98 (bs, 1H), 3.56-3.45 (m, 1H), 3.30-3.20 (m, 2H), 3.10-3.0 (m, 0.5H), 2.90-2.82 (m, 0.5H), 2.75-2.60 (m, 2H), 2.40-2.30 (m, 2H), 2.22 (d, J=6.9 Hz, 1H), 2.17 (d, J=6.8 Hz, 1H), 2.15-2.08 (m, 2H), 1.95-1.75 (m, 2H), 1.74-1.65 (m, 2H), 1.65-1.50 (m, 2H); Mass (m/z): 198 (M+H)⁺.

Preparation 7: Preparation of 1-(3-methoxy propyl)piperidin-4-carboxylic acid

Step (i): Preparation of ethyl 1-(3-methoxy propyl)piperidin-4-carboxylate

To a stirred solution of ethyl isonipecotate (22.0 grams, 140 mmol) in acetonitrile (250 mL) at room temperature was added cesium carbonate (97 grams, 298 mmol) followed by 1-bromo-3-methoxypropane (20 mL, 154 mmol) and the reaction mixture was heated to reflux for 4 hours. The reaction mixture was cooled to room temperature and filtered through a small pad of celite. The volatiles were removed under reduced pressure to obtain ethyl 1-(3-methoxy propyl)piperidin-4-carboxylate (31.0 grams).

Yield: 99%.

$^1$H-NMR (CDCl$_3$): δ 4.12 (q, 2H), 3.41 (t, J=6.4 Hz, 2H), 2.90-2.85 (m, 2H), 2.38 (t, J=7.4 Hz, 2H), 2.34-2.20 (m, 1H), 2.05-1.93 (m, 2H), 1.92-1.85 (m, 2H), 1.80-1.70 (m, 4H), 1.23 (t, J=7.1 Hz, 3H);

Mass (m/z): 230 (M+H)$^+$.

Step (ii): Preparation of 1-(3-methoxy propyl)piperidin-4-carboxylic acid

To a stirred mixture of ethyl 1-(3-methoxy propyl)piperidin-4-carboxylate (33.0 grams, 144.1 mmol, obtained in the above step), tetrahydrofuran (200 mL) and water (200 mL) was added lithium hydroxide monohydrate (6.1 grams, 144.1 mmol). The reaction mixture was stirred at room temperature for 16 hours before being diluted with ethylacetate. The two layers were separated and the aqueous layer was acidified to pH: 3-4 with concentrated hydrochloric acid and the volatiles were removed under reduced pressure to obtain 1-(3-methoxy propyl)piperidin-4-carboxylic acid (35.0 grams).

Yield: 100%.

$^1$H-NMR (DMSO-d$_6$): δ 3.30 (t, J=6.4 Hz, 2H), 3.19 (s, 3H), 2.80-2.70 (m, 2H), 2.25 (t, J=7.5 Hz, 2H), 2.15-2.05 (m, 1H), 1.92-1.82 (m, 2H), 1.78-1.70 (m, 2H), 1.68-1.57 (m, 2H), 1.55-1.43 (m, 2H);

Mass (m/z): 202 (M+H)$^+$.

Preparation 8: Preparation of 3-cyclobutyl-3-aza bicyclo[3.1.0]hexane-6-carboxylic acid

Step (i): Preparation of ethyl 3-benzyl-3-aza bicyclo[3.1.0]hexane-6-carboxylate To a stirred solution of ethyl 3-benzyl-2,4-dioxo-3-aza bicyclo[3.1.0]hexane-6-carboxylate (*SYNLETT*, 1996, 1097; 5.0 grams, 18.3 mmol) in tetrahydrofuran (74 mL) cooled at 0° C., BH$_3$-DMS (2N solution in tetrahydrofuran 36 mL, 73.2 mmol) was added over a period of 30 minutes. The reaction temperature was gradually raised to reflux for 6 hours. After cooling the reaction mixture to 0° C., it was quenched by adding aqueous ammonium chloride solution and was extracted with ethyl acetate. The combined organic layer was dried over anhydrous sodium sulphate and the solvent was removed under reduced pressure. The crude product was purified by silica gel column chromatography to obtain ethyl 3-benzyl-3-aza bicyclo[3.1.0]hexane-6-carboxylate (2.8 grams)

Yield: 62.5%

$^1$H-NMR (CDCl$_3$): δ 7.40-7.20 (m, 5H), 4.14 (q, 2H), 3.61 (s, 2H), 3.05 (d, J=9.0 Hz, 2H), 2.44 (d, J=8.7 Hz, 2H), 2.14 (t, J=2.6 Hz, 1H), 1.97 (s, 2H), 1.28 (t, J=7.1 Hz, 3H).

Mass (m/z): 246.2 (M+H)$^+$.

Step (ii): Preparation of ethyl 3-aza bicyclo[3.1.0]hexane-6-carboxylate

To a stirred solution of ethyl 3-benzyl-3-aza bicyclo[3.1.0]hexane-6-carboxylate (2.0 grams, 8.1 mmol, obtained in the above step) in methanol (20 mL), palladium hydroxide (468 mg) was added. The reaction mixture was applied with hydrogen pressure using hydrogen balloon. The reaction mixture was stirred at room temperature for 2 hours and filtered through a small pad of celite. The volatiles were removed under reduced pressure to obtain ethyl 3-aza bicyclo[3.1.0] hexane-6-carboxylate (1.22 grams)

Yield: 96%.

$^1$H-NMR (CDCl$_3$): δ 4.11 (q, 2H), 3.11 (d, J=11.6 Hz, 2H), 2.98 (d, J=11.7 Hz, 2H), 2.02 (s, 2H), 1.49 (t, J=3.0 Hz, 1H), 1.24 (t, J=4.2 Hz, 3H); Mass (m/z): 156.1 (M+H)$^+$.

Step (iii): Preparation of ethyl 3-cyclobutyl-3-aza bicyclo[3.1.0]hexane-6-carboxylate A mixture of cyclobutanone (157 mg, 2.19 mmol) in acetic acid (0.11 mL, 1.56 mmol) was added to a stirred solution of ethyl 3-aza bicyclo[3.1.0]hexane-6-carboxylate (243 mg, 1.56 mmol, obtained in the above step) in dichloromethane, cooled at 0° C. Solid sodium triacetoxy borohydride (727 mg, 3.43 mmol) was added portion wise over a period of 15 minutes. The reaction mixture was gradually warmed to room temperature and stirred for 16 hours. The reaction mixture was cooled to 0° C. and basified with saturated sodium bicarbonate solution (pH: 7.5). The two layers were separated, the organic layer was washed with brine, dried over anhydrous sodium sulfate and the volatiles were removed under reduced pressure to obtain ethyl 3-cyclobutyl-3-aza bicyclo[3.1.0] hexane-6-carboxylate (219 mg).

Yield: 66.0%.

$^1$H-NMR (CDCl$_3$): δ 4.11 (q, 2H), 3.10-2.90 (m, 3H), 2.34 (d, J=8.8 Hz, 2H), 2.04 (s, 1H), 1.93 (s, 2H), 2.0-1.80 (m, 3H), 1.80-1.55 (m, 3H), 1.25 (t, J=7.1 Hz, 3H);

Mass (m/z): 210.2 (M+H)$^+$.

Step (iv): Preparation of 3-cyclobutyl-3-aza bicyclo[3.1.0]hexane-6-carboxylic acid To a stirred mixture of ethyl 3-cyclobutyl-3-aza bicyclo [3.1.0]hexane-6-carboxylate (218 mg, 1.04 mmol, obtained in the above step), tetrahydrofuran (2 mL) and water (2.0 mL) cooled at 0° C., lithium hydroxide monohydrate (133 mg, 3.19 mmol) was added in a single lot. The reaction mixture was stirred at room temperature for 24 hours. The reaction mixture was cooled again to 0° C. and acidified with 2N hydrochloric acid to pH: 2-3. The volatiles were removed under reduced pressure and the traces of water were removed by azeotropic distillation with toluene to obtain 3-cyclobutyl-3-aza bicyclo[3.1.0]hexane-6-carboxylic acid (180 mg).

Yield: 92%.

$^1$H-NMR (DMSO-d$_6$): δ 2.98-2.86 (m, 1H), 2.78 (d, J=8.5 Hz, 2H), 2.20 (d, J=8.1 Hz, 2H), 1.90-1.80 (m, 2H), 1.82-1.68 (m, 2H), 1.65-1.55 (m, 2H), 1.49 (s, 2H), 1.42 (s, 1H);

Mass (m/z): 182.3 (M+H)$^+$.

Preparation 9: Preparation of [1,4']Bipiperidinyl-4,1'-dicarboxylic acid 1'-ethyl ester

Step (i): Preparation of ethyl 4-oxo piperidine-1-carboxylate

To the stirred solution of piperidin-4-one hydrochloride (2.0 g, 14.7 mmol) in DCM (60 mL) cooled at 0° C., was added triethylamine (5.15 mL, 36.75 mmol) and ethylchloroformate (1.59 mL, 16.6 mml). The reaction mixture was stirred at room temperature for 2 hours before being diluted with water. The two layers were separated, the organic layer was dried over anhydrous sodium sulfate and the volatiles were removed under reduced pressure to obtain ethyl 4-oxo-piperidine-1-carboxylate (3.14 grams).

Yield: 98%

$^1$H-NMR (CDCl$_3$): δ 4.22 (q, 2H), 3.79 (t, J=6.0 Hz, 2H), 2.48 (t, J=6.0 Hz, 2H), 1.31 (t, J=7.1 Hz, 3H);

Mass (m/z): 172.1 (M+H)$^+$.

Step (ii): Preparation of [1,4']Bipiperidinyl-4,1'-dicarboxylic acid diethyl ester A mixture of ethyl 4-oxo piperidine-1-carboxylate (3.14 grams, 18.3 mmol, obtained in the above step) in acetic acid (1.05 mL, 18.3 mmol) was added to a stirred solution of ethyl isonipecotate (2.87 mL, 18.3 mmol) in dichloromethane (10 mL) cooled at 0° C. Solid sodium triacetoxy borohydride (11.6 grams, 54.9 mmol) was added portion wise over a period of 15 minutes. The reaction mixture was gradually warmed to room temperature and stirred for 16 hours. The reaction mixture was cooled to 0° C. and basified with saturated sodium bicarbonate solution (pH 7.5). The two layers were separated, the organic layer was washed with brine, dried over anhydrous sodium sulfate and the volatiles were removed under reduced pressure. The crude product was purified by silica gel column chromatography to obtain [1,4'] Bipiperidinyl-4,1'-dicarboxylic acid diethyl ester (5.51 grams).

Yield: 96.3%.

$^1$H-NMR (CDCl$_3$): δ 5.60-5.10 (m, 2H), 4.35-4.15 (m, 1H), 4.20-4.08 (m, 4H), 3.98-3.85 (m, 1H), 3.20-3.10 (m, 1H), 3.10-3.0 (m, 1H), 2.86-2.70 (m, 2H), 2.60-2.50 (m, 1H), 2.48-2.35 (m, 1H), 2.10-2.0 (m, 2H), 1.98-1.85 (m, 4H), 1.60-1.43 (m, 2H), 1.32-1.22 (m, 6H);

Mass (m/z): 313.2 (M+14)$^+$.

Step (iii): Preparation of [1,4']Bipiperidinyl-4,1'-dicarboxylic acid 1'-ethyl ester To a stirred mixture of [1,4']Bipiperidinyl-4,1'-dicarboxylic acid diethyl ester (5.51 grams, 17.67 mmol), tetrahydrofuran (34 mL) and water (34 mL) cooled at 0° C., lithium hydroxide monohydrate (742.0 mg, 17.67 mml) was added. The reaction mixture was stirred at room temperature for 16 hours, diluted with Ethyl acetate. The two layers were separated, the aqueous layer was acidified with 2N hydrochloric acid to pH: 3-4 and the volatiles were removed under reduced pressure to obtain [1,4']Bipiperidinyl-4,1'-dicarboxylic acid 1'-ethyl ester (5.0 grams).

Yield: 94%

$^1$H-NMR (DMSO-d$_6$): δ 12.53 (bs, 1H), 11.16 (bs, 1H), 4.15-3.98 (m, 4H), 3.47-3.35 (m, 3H), 3.0-2.90 (m, 2H), 2.90-2.65 (m, 2H), 2.60-2.50 (m, 1H), 2.18-2.08 (m, 2H), 2.05-1.94 (m, 4H), 1.60-1.50 (m, 2H), 1.16 (t, =7.0 Hz, 3H);

Mass (m/z): 285.1 (M+H)$^+$.

Example 1

Preparation of 6-Chloro-8-[5-(1-cyclopropyl-piperidin-4-yl)-[1,3,4]oxadiazol-2-yl]-chroman-5-ylamine hemi fumarate

Step (i): Preparation of N-(1-cyclopropyl piperidine-4-carbonyl)-N'-(5-amino-6-chloro chroman-8-carbonyl) hydrazine To a stirred solution of 5-amino-6-chloro chroman-8-carboxylic acid hydrazide (8.0 grams, 33.1 mmol, obtained in preparation 1) in dichloromethane (200 mL) cooled at 0° C., was added triethylamine (13.9 mL, 99.9 mmol) and a solution of 1-cyclopropylpiperidine-4-carbonyl chloride (11.0 grams) in dichloromethane (200 mL). The reaction mixture was warmed to room temperature and stirred for 16 hours before diluting it with water (160 mL). The two layers were separated, the organic layer was dried over anhydrous sodium sulphate and the volatiles were removed under reduced pressure to obtain the title compound (10.5 grams).

Yield: 81%.

$^1$H-NMR (DMSO-d$_6$): δ 10.16 (d, J=3.2 Hz, 1H), 9.64 (d, J=3.2 Hz, 1H), 7.58 (s, 1H), 5.73 (bs, 2H), 4.21 (t, J=4.7 Hz, 2H), 3.0-2.88 (m, 2H), 2.46 (t, J=6.5 Hz, 2H), 2.30-2.20 (m, 1H), 2.18-2.05 (m, 2H), 2.0-1.90 (m, 2H), 1.70-1.60 (m, 2H), 1.60-1.42 (m, 3H), 0.42-0.35 (m, 2H), 0.30-0.22 (m, 2H);

Mass (m/z): 393, 395 (M+H)$^+$.

Step (ii): Preparation of 6-chloro-8-[5-(1-cyclopropyl piperidin-4-yl)-[1,3,4]oxadiazol-2-yl]-chroman-5-ylamine To N-(1-cyclopropyl piperidine-4-carbonyl)-N'-(5-amino-6-chloro chroman-8-carbonyl) hydrazine (10.5 grams, 26.7 mmol, obtained in the above step) was added phosphoryl chloride (53.5 mL). The reaction temperature was gradually raised to 120° C. The reaction mixture was stirred at this temperature for 1 h, cooled to room temperature and triturated with hexanes (3×100 mL). The crude reaction was diluted with 10% aqueous sodium bicarbonate solution and extracted with a 1:9 mixture of methanol in dichloromethane. The organic layer was dried over anhydrous sodium sulphate and solvent was removed under reduced pressure and the crude product was purified by silica gel column to obtain 6-Chloro-8-[5-(1-cyclopropyl piperidin-4-yl)-[1,3,4]oxadiazol-2-yl] chroman-5-yl amine (8.8 grams).

Yield: 87.9%.

$^1$H-NMR (CDCl$_3$): δ 7.66 (s, 1H), 4.35 (bs, 2H), 4.28 (t, J=5.0 Hz, 2H), 3.18-3.10 (m, 2H), 3.08-2.93 (m, 1H), 2.53 (t, J=6.6 Hz, 2H), 2.40-2.30 (m, 2H), 2.18-2.05 (m, 4H), 2.0-1.87 (m, 2H), 1.70-1.60 (m, 1H), 0.50-0.40 (m, 4H); Mass (m/z): 375, 377 (M+H)$^+$.

Step (iii): Preparation of 6-chloro-8-[5-(1-cyclopropyl piperidin-4-yl)-[1,3,4]oxadiazol-2-yl]chroman-5-yl amine hemi fumarate A suspension of 6-chloro-8-[5-(1-cyclopropyl piperidin-4-yl)-[1,3,4]oxadiazol-2-yl]chroman-5-yl amine (14 grams, 37.3 mmol, obtained in the above step) in ethanol (280 mL) was heated to reflux until clear solution obtained. The mixture was cooled to room temperature and fumaric acid (4.32 grams, 37.3 mmol) was added. The reaction mixture was heated to reflux for 1 hour. The volatiles were removed under reduced pressure and the furmarate salt, thus obtained, was recrystallized from isopropanol to obtain 6-Chloro-8-[5-(1-cyclopropyl piperidin-4-yl)-[1,3,4]oxadiazol-2-yl]chroman-5-yl amine hemi fumarate (14.0 grams).

Yield: 92.8%.

$^1$H-NMR (DMSO-d$_6$): δ 7.48 (s, 1H), 6.60 (s, 1H), 5.75 (s, 2H), 4.13 (t, J=4.8 Hz, 2H), 3.0-2.90 (m, 3H), 2.52-2.42 (m, 2H), 2.40-2.30 (m, 2H), 2.01-1.90 (m, 4H), 1.75-1.62 (m, 3H), 0.48-0.40 (m, 2H), 0.35-0.28 (m, 2H); Mass (m/z): 375, 377 (M+H)$^+$.

Example 2

Preparation of 6-Chloro-8-[5-(1-cyclobutyl piperidin-4-ylmethyl)-[1,3,4]oxadiazol-2-yl]-chroman-5-yl amine L(+)-tartarate salt Step (i): Preparation of 6-chloro-8-[5-(1-cyclobutyl piperidin-4-yl methyl)-[1,3,4]oxadiazol-2-yl]-chroman-5-yl amine To the (1-cyclobutyl piperidin-4-yl) acetic acid (725 mg, 3.52 mmol, obtained in preparation 4) was added phosphoryl chloride (4 mL). The mixture was stirred for 15 minutes and 5-Amino-6-chloro-chroman-8-carboxylic acid hydrazide (500 mg, 2.0 mmol) was added. The reaction mixture was gradually heated to reflux for 30 minutes. The reaction mixture was cooled to room temperature, triturated with hexanes (2×20 mL) and the crude mass was basified with aqueous sodium bicarbonate solution. The basified mixture was extracted with 10% methanol in dichloromethane. The organic layer was dried over anhydrous sodium sulphate and the solvent was removed under reduced pressure and was purified by silica gel column to obtain 6-chloro-8-[5-(1-cyclobutyl piperidin-4-ylmethyl)-[1,3,4]oxadiazol-2-yl]chroman-5-yl amine (250 mg). Yield: 30%.

$^1$H-NMR (CDCl$_3$): δ 7.68 (s, 1H), 4.35 (bs, 2H), 4.28 (t, J=5.0 Hz, 2H), 2.93-2.88 (m, 2H), 2.83 (d, J=6.9 Hz, 2H), 2.73-2.62 (m, 1H), 2.54 (t, J=6.6 Hz, 2H), 2.20-2.10 (m, 2H), 2.08-2.0 (m, 2H), 1.95-1.65 (m, 9H), 1.48-1.35 (m, 2H);

Mass (m/z): 403, 405 (M+H)$^+$.

Step (ii): Preparation of 6-chloro-8-[5-(1-cyclobutyl piperidin-4-yl methyl)-[1,3,4]oxadiazol-2-yl]-chroman-5-yl amine L(+)-tartarate salt To a stirred solution of 6-chloro-8-[5-(1-cyclobutyl piperidin-4-yl methyl)-[1,3,4]oxadiazol-2-yl]chroman-5-yl amine (175.7 mg, 0.436 mmol, obtained in the above step) in methanol (2 mL), L(+)-tartaric acid (65.4 mg, 0.436 mmol) was added. The reaction mixture was stirred for 1 hour at room temperature and the volatiles were removed under reduced pressure to obtain a crude mass which was triturated several times with solvent ether to obtain 6-chloro-8-[5-(1-cyclobutyl piperidin-4-yl methyl)-[1,3,4]oxadiazol-2-yl]chroman-5-yl amine L(+)-tartarate (206.2 mg)

Yield: 85.5%

$^1$H-NMR (DMSO-d$_6$): δ 7.46 (s, 1H), 5.79 (bs, 2H), 4.12 (t, J=4.7 Hz, 2H), 4.06 (bs, 2H), 3.20-3.10 (m, 1H), 3.10-3.0 (m, 2H), 2.84 (d, J=6.7 Hz, 2H), 2.48 (t, J=7.6 Hz, 2H), 2.33-2.15 (m, 2H), 2.10-2.0 (m, 2H), 2.0-1.85 (5H), 1.85-1.72 (m, 2H), 1.70-1.58 (m, 2H), 1.45-1.30 (m, 2H); Mass (m/z): 403, 405 (M+H)$^+$.

Example 3

Preparation of 1-isopropyl-3-{5-[1-(3-methoxy propyl)piperidin-4-yl]-[1,3,4]oxadiazol-2-yl}-1H-indazole oxalate salt Step (i): Preparation of 1-isopropyl-3-{5-[1-(3-methoxy propyl)piperidin-4-yl]-[1,3,4]oxadiazol-2-yl}-1H-indazole To the mixture of 1-isopropyl-1H-indazole-3-carboxylic acid hydrazide (15.0 grams, 68.8 mmol) and 1-(3-Methoxy propyl)-piperidine-4-carboxylic acid hydrochloride (20.9 grams, 88.2 mmol, obtained in preparation 7) cooled at 0° C. was added phosphoryl chloride (130 mL). The reaction temperature was gradually raised to 100° C. and stirred was 2 hours. Upon completion of the reaction, it was cooled to 0° C. and triturated with hexanes (3×250 mL). The crude product was basified with aqueous sodium hydroxide solution and extracted with 5% methanol in dichloromethane. The combined organic layer was dried over anhydrous sodium sulphate and the solvent was removed under reduced pressure. The crude product was purified by silica gel column chromatography to obtain 1-isopropyl-3-{5-[1-(3-methoxy propyl)piperidin-4-yl]-[1,3,4]oxadiazol-2-yl}-1H-indazole (15.78 grams)

Yield: 59%.

$^1$H-NMR (CDCl$_3$): δ 8.35 (d, J=8.1 Hz, 1H), 7.53 (d, J=8.5 Hz, 1H), 7.47 (t, J=7.0 Hz, 1H), 7.33 (t, J=7.4 Hz, 1H), 5.05-4.90 (m, 1H), 3.44 (t, J=6.4 Hz, 2H), 3.35 (s, 3H), 3.15-2.97 (m, 3H), 2.48 (t, J=7.3 Hz, 2H), 2.26-2.02 (m, 6H), 1.88-1.75 (m, 2H), 1.67 (d, J=6.7 Hz, 6H);

Mass (m/z): 384.5 (M+H)$^+$.

Step (ii): Preparation of 1-Isopropyl-3-{5-[1-(3-methoxy-propyl)-piperidin-4-yl]-[1,3,4]oxadiazol-2-yl}-1H-indazole oxalate salt To a stirred solution of 1-isopropyl-3-{5-[1-(3-methoxy propyl)piperidin-4-yl]-[1,3,4]oxadiazol-2-yl}-1H-indazole (12.55 grams, 32.7 mmol, obtained in the above step) in 2-propanol (200 mL); oxalic acid (4.12 grams, 32.7 mmol) was added. After stirring at room temperature for 1 hour the reaction was further diluted with 2-propanol and refluxed for 2 hours. The crystalline product which was precipitated after cooling the reaction mixture to room temperature was filtered, dried under vacuum to obtain 1-isopropyl-3-{5-[1-(3-methoxy propyl)piperidin-4-yl]-[1,3,4]oxadiazol-2-yl}-1H-indazole oxalate salt (16.4 grams)

Yield: 88%

$^1$H-NMR (DMSO-d$_6$): δ 8.18 (d, J=8.1 Hz, 1H), 7.90 (d, J=8.5 Hz, 1H), 7.54 (t, J 7.4 Hz, 1H), 7.38 (t, J=7.7 Hz, 1H), 5.23-5.10 (m, 1H), 3.50-3.40 (m, 3H), 3.37 (t, J=5.9 Hz, 2H), 3.23 (s, 3H), 3.10-2.96 (m, 4H), 2.35-2.25 (m, 2H), 2.18-2.02 (m, 2H), 1.94-1.85 (m, 2H), 1.53 (d, J=6.6 Hz, 6H);

Mass (m/z): 384.3 (M+H)$^+$.

Example 4

Preparation of 3-[5-(1-cyclobutyl-piperidin-4-yl methyl)-[1,3,4]oxadiazol-2-yl]-1-isopropyl-1H-indazole L(+)-tartarate salt Step (i): Preparation of 3-[5-(1-cyclobutyl-piperidin-4-yl methyl)-[1,3,4]oxadiazol-2-yl]-1-isopropyl-1H-indazole To the mixture of 1-isopropyl-1H-indazole-3-carboxylic acid hydrazide (120 mg, 0.55 mmol) and (1-cyclobutyl piperidin-4-yl) acetic acid hydrochloride (147 mg, 0.74 mmol, obtained in preparation 6) cooled at 0° C., was added phosphoryl chloride (1.5 mL). The reaction temperature was gradually raised to 100° C. and stirred was 2 hours. Upon completion of the reaction, it was cooled to 0° C. and triturated with hexanes (3×25 mL). The crude product was cooled to 0° C., basified with aqueous sodium hydroxide solution and extracted with 5% methanol in dichloromethane. The combined organic layer was dried over anhydrous sodium sulphate and the solvent was removed under reduced pressure. The crude product was purified by silica gel column chromatography to obtain 3-[5-(1-cyclobutyl piperidin-4-yl methyl)-[1,3,4]oxadiazol-2-yl]-1-isopropyl-1H-indazole (62 mg)

Yield: 30%

¹H-NMR (CDCl₃): δ 8.37 (d, J=8.1 Hz, 1H), 7.54 (d, J=8.5 Hz, 1H), 7.48 (t, J=6.9 Hz, 1H), 7.35 (t, J=7.5 Hz, 1H), 5.08-4.92 (m, 1H), 2.93 (d, J=7.1 Hz, 2H), 2.92-2.87 (m, 2H), 2.74-2.62 (m, 1H), 2.10-1.93 (m, 3H), 1.92-1.82 (m, 4H), 1.80-1.65 (m, 4H), 1.68 (d, J=6.7 Hz, 6H), 1.52-1.40 (m, 2H);

Mass (m/z): 380.2 (M+H)⁺.

Step (ii): Preparation of 3-[5-(1-cyclobutyl piperidin-4-yl methyl)-[1,3,4]oxadiazol-2-yl]-1-isopropyl-1H-indazole L(+)-tartarate salt To a stirred solution of 3-[5-(1-cyclobutyl piperidin-4-yl methyl)-[1,3,4]oxadiazol-2-yl]-1-isopropyl-1H-indazole (62 mg, 0.16 mmol, obtained in the above step) in 2-propanol (5.0 mL), L(+)-tartaric acid (26 mg, 0.16 mmol) was added. After stirring at room for 1 hour the volatiles were removed under reduced pressure and the crude product was triturated several times with ether to obtain 3-[5-(1-cyclobutyl piperidin-4-yl methyl)-[1,3,4]oxadiazol-2-yl]-1-isopropyl-1H-indazole L(+)-tartarate salt (81 mg) Yield: 94%

¹H-NMR (DMSO-d₆): δ 8.18 (d, J=8.1 Hz, 1H), 7.90 (d, J=8.5 Hz, 1H), 7.54 (t, J 7.4 Hz, 1H), 7.38 (t, J=7.6 Hz, 1H), 5.22-5.10 (m, 1H), 4.11 (s, 2H), 3.30-3.20 (m, 2H), 3.20-3.05 (m, 2H), 3.0 (d, J=6.8 Hz, 2H), 2.45-2.30 (m, 1H), 2.10-1.90 (m, 4H), 1.90-1.80 (m, 2H), 1.78-1.65 (m, 2H), 1.50-1.40 (m, 2H);

Mass (m/z): 380.2 (M+H)⁺.

Example 5

Preparation of 6-chloro-8-[5-(3-cyclobutyl-3-aza bicyclo[3.1.0]hex-6-yl)-[1,3,4]oxadiazol-2-yl]chroman-5-ylamine oxalic acid Step (i): Preparation of 6-chloro-8-[5-(3-cyclobutyl-3-aza bicyclo[3.1.0]hex-6-yl)-[1,3,4]oxadiazol-2-yl]chroman-5-yl amine To 3-cyclobutyl-3-aza bicyclo[3.1.0]hexane-6-carboxylic acid (74 mg, 0.40 mmol, obtained in preparation 8) was added phosphoryl chloride (1 mL). The mixture was stirred for 15 minutes and 5-amino-6-chloro chroman-8-carboxylic acid hydrazide (80 mg, 0.33 mmol) was added. The reaction mixture was gradually heated to reflux for 1 hour. The reaction mixture was cooled to room temperature, triturated with hexanes (2×20 mL) and the crude mass was basified with aqueous sodium bicarbonate solution. The basified mixture was extracted with 10% methanol in dichloromethane The organic layer was dried over anhydrous sodium sulphate and the solvent was removed under reduced pressure and was purified by silica gel column to obtain 6-chloro-8-[5-(3-cyclobutyl-3-aza bicyclo[3.1.0]hex-6-yl)-[1,3,4]oxadiazol-2-yl]chroman-5-yl amine (18 mg).

Yield: 14.0%.

¹H-NMR (CDCl₃): δ 7.64 (s, 1H), 4.33 (bs, 2H), 4.27 (t, J=5.3 Hz, 2H), 3.20-3.0 (m, 3H), 2.70-2.60 (m, 1H), 2.53 (t, J=6.4 Hz, 2H), 2.48-2.35 (m, 2H), 2.20-2.10 (m, 4H), 2.0-1.90 (m, 2H), 1.90-1.80 (m, 1H), 1.80-1.60 (m, 2H), 1.30-1.20 (m, 1H).

Mass (m/z): 387.1, 389.2 (M+H)⁺

Step (ii): Preparation of 6-chloro-8-[5-(3-cyclobutyl-3-aza bicyclo[3.1.0]hex-6-yl)-[1,3,4]oxadiazol-2-yl] chroman-5-yl amine oxalate salt To a stirred solution of 6-chloro-8-[5-(3-cyclobutyl-3-aza bicyclo[3.1.0]hex-6-yl)-[1,3,4]oxadiazol-2-yl]chroman-5-yl amine (18 mg, 0.05 mmol, obtained in the above step) in 2-propanol (3 mL), oxalic acid (6.0 mg, 0.05 mmol) was added. After stirring at room temperature for 1 hour the reaction was further diluted with 2-propanol and refluxed for 2 hours. The volatiles were removed under reduced pressure and the crude product which was obtained was triturated with ether, dried under vacuum to obtain 6-Chloro-8-[5-(3-cyclobutyl-3-aza bicyclo[3.1.0]hex-6-yl)-[1,3,4]oxadiazol-2-yl]chroman-5-yl amine oxalate salt (21.2 mg)

Yield: 95.6%

¹H-NMR (DMSO-d₆): δ 7.47 (s, 1H), 5.80 (bs, 2H), 4.28 (t, J=5.3 Hz, 2H), 3.80-3.55 (m, 2H), 3.30-3.20 (m, 1H), 2.70-2.60 (m, 1H), 2.60-2.40 (m, 4H), 2.30-2.05 (m, 4H), 2.0-1.90 (m, 3H), 1.90-1.70 (m, 2H), 1.30-1.20 (m, 1H); Mass (m/z): 387.1, 389.2 (M+H)⁺.

Example 6

Preparation of 4-[5-(8-Amino-7-chloro-2,3-dihydro benzo[1,4]dioxan-5-yl)-[1,3,4]oxadiazol-2-yl]-[1,4'] bipiperidinyl-1'-carboxylic acid ethyl ester oxalate salt Step (i): Preparation of 4-[5-(8-Amino-7-chloro-2,3-dihydro benzo[1,4]dioxan-5-yl)-[1,3,4]oxadiazol-2-yl]-[1,4']bipiperidinyl-1'-carboxylic acid ethyl ester To the [1,4']bipiperidinyl-4,1'-dicarboxylic acid 1'-ethyl ester (372 mg, 1.02 mmol, obtained in preparation 9) was added phosphoryl chloride (3.2 mL). The mixture was stirred for 15 minutes and 8-amino-7-chloro-2,3-dihydro benzo[1,4] dioxane-5-carboxylic acid hydrazide (200 mg, 0.82 mmol) was added. The reaction mixture was gradually heated to reflux for 1 hour. The reaction mixture was cooled to room temperature, triturated with hexanes (2×50 mL) and the crude mass was basified with aqueous sodium bicarbonate solution. The basified mixture was extracted with ethyl acetate. The organic layer was dried over anhydrous sodium sulphate and the solvent was removed under reduced pressure and was purified by silica gel column to obtain 4-[5-(8-amino-7-chloro-2,3-dihydro benzo[1,4]dioxan-5-yl)-[1,3,4]oxadiazol-2-yl]-[1,4']bipiperidinyl-1'-carboxylic acid ethyl ester (110 mg).

Yield: 27.5%.

¹H-NMR (CDCl₃): δ 7.42 (s, 1H), 4.50-4.36 (m, 6H), 4.33-4.20 (m, 2H), 4.12 (q, 2H), 3.03-2.92 (m, 3H), 2.83-2.70 (m, 2H), 2.55-2.42 (m, 1H), 2.42-2.30 (m, 2H), 2.15-2.06 (m, 2H), 2.04-1.90 (m, 2H), 1.86-1.78 (m, 2H), 1.55-1.40 (m, 2H), 1.26 (t, J=7.1 Hz, 3H);

Mass (m/z): 492.1, 494.3 (M+H)⁺

Step (ii): Preparation of 4-[5-(8-amino-7-chloro-2,3-dihydro benzo[1,4]dioxin-5-yl)-[1,3,4]oxadiazol-2-yl]-[1,4']bipiperidinyl-1'-carboxylic acid ethyl ester oxalate salt To a stirred solution of 4-[5-(8-amino-7-chloro-2,3-dihydro benzo[1,4]dioxin-5-yl)-[1,3,4]oxadiazol-2-yl]-[1,4']bipiperidinyl-1'-carboxylic acid ethyl ester (100 mg, 0.20 mmol, obtained in the above step) in ethanol (3 mL), oxalic acid (23 mg, 0.18 mmol) was added. After stirring at room temperature for 1 hour the reaction was further diluted with 2-propanol and refluxed for 2 hours. The volatiles were removed under reduced pressure and the crude product obtained was triturated with ether and dried under vacuum to obtain 4-[5-(8-amino-7-chloro-2,3-dihydro benzo[1,4]dioxin-5-yl)-[1,3,4]oxadiazol-2-yl]-[1,4']bipiperidinyl-1'-carboxylic acid ethyl ester oxalate salt (115 mg)

Yield: 97.4%

$^1$H-NMR (DMSO-d$_6$): δ 7.29 (s, 1H), 5.66 (bs, 2H), 4.33 (s, 4H), 4.15-4.05 (m, 2H), 4.03 (q, 2H), 3.40-3.15 (m, 4H), 3.10-2.90 (m, 2H), 2.90-2.70 (m, 2H), 2.26-2.18 (m, 2H), 2.08-1.90 (m, 4H), 1.58-1.42 (m, 2H), 1.17 (t, J=7.0 Hz, 3H); Mass (m/z): 492.1, 494.3 (M+H)$^+$.

Example 7

Preparation of 5-Chloro-7-{5-[1-(tetrahydro pyran-4-yl) piperidin-4-yl]-[1,3,4]oxadiazol-2-yl}-2,3-dihydro benzofuran-4-yl amine oxalate salt Step (i): Preparation of 5-Chloro-7-{5-[1-(tetrahydro pyran-4-yl) piperidin-4-yl]-[1,3,4]oxadiazol-2-yl}-2,3-dihydro benzofuran-4-yl amine To 1-(tetrahydro pyran-4-yl) piperidine-4-carboxylic acid (168.2 mg, 0.58 mmol) was added phosphoryl chloride (1.76 mL). The mixture was stirred for 15 minutes and 4-amino-5-chloro-2,3-dihydro benzofuran-7-carboxylic acid hydrazide (101.2 mg, 0.0.44 mmol, obtained in preparation 3) was added. The reaction mixture was gradually heated to reflux for 2 hours. The reaction mixture was cooled to room temperature, triturated with hexanes (2×20 mL) and the crude mass was basified with aqueous sodium bicarbonate solution. The basified mixture was extracted with 10% methanol in dichloromethane. The organic layer was dried over anhydrous sodium sulphate and the solvent was removed under reduced pressure. The residual mass was purified by silica gel column to obtain 5-chloro-7-{5-[1-(tetrahydro pyran-4-yl) piperidin-4-yl]-[1,3,4]oxadiazol-2-yl}-2,3-dihydro benzofuran-4-yl amine (23.5 mg).

Yield: 13.1%.

$^1$H-NMR (CDCl$_3$): δ 7.64 (s, 1H), 4.84 (t, J=8.7 Hz, 2H), 4.31 (bs, 2H), 4.10-4.0 (m, 2H), 3.39 (t, J=11.4 Hz, 2H), 3.10 (t, J=8.7 Hz, 2H), 3.10-2.95 (m, 3H), 2.62-2.50 (m, 1H), 2.45-2.25 (m, 2H), 2.20-1.95 (m, 4H), 1.88-1.75 (m, 2H), 1.75-1.60 (m, 2H);
Mass (m/z): 405.2, 407.4 (M+H)$^+$.

Step (ii): Preparation of 5-chloro-7-{5-[1-(tetrahydro pyran-4-yl) piperidin-4-yl]-[1,3,4]oxadiazol-2-yl}-2,3-dihydro benzofuran-4-yl amine oxalate salt To a stirred solution of 5-chloro-7-{5-[1-(tetrahydro pyran-4-yl) piperidin-4-yl]-[1,3,4]oxadiazol-2-yl}-2,3-dihydro benzofuran-4-ylamine (20.4 mg, 0.05 mmol) in ethanol (2 mL), oxalic acid (6.0 mg, 0.05 mmol) was added. After stirring at room temperature for 1 hour the reaction was further diluted with 2-propanol and refluxed for 2 hour; The volatiles were removed under reduced pressure and the crude product obtained was triturated with ether, dried under vacuum to obtain 5-chloro-7-{5-[1-(tetrahydro pyran-4-yl) piperidin-4-yl]-[1,3,4]oxadiazol-2-yl}-2,3-dihydro benzofuran-4-ylamine oxalate salt (22.5 mg).

Yield: 90.3%

$^1$H-NMR (DMSO-d$_6$): δ 7.49 (s, 1H), 6.04 (s, 2H), 4.68 (t, J=8.7 Hz, 2H), 4.0-3.90 (m, 2H), 3.40-3.20 (m, 5H), 3.0 (t, = 8.7 Hz, 2H), 2.35-2.20 (m, 3H), 2.10-1.90 (m, 5H), 1.70-1.57 (m, 3H);
Mass (m/z): 405.1, 407.2 (M+H)$^+$.

Examples 8-49

The compounds of Examples 8-49 were prepared by following the procedures as described in Examples 1 to 7, with some non-critical variations

| | | |
|---|---|---|
| 8. | 6-Chloro-8-{5-[1-(2-methoxy-ethyl)-piperidin-4-yl]-[1,3,4]oxadiazol-2-yl}-chroman-5-ylamine | $^1$H-NMR (DMSO-d$_6$): δ 9.92 (bs, 1H), 7.49 (s, 1H), 4.13 (bs, 2H), 3.70 (t, J=5.0 Hz, 2H), 3.54 (t, J = 5.5 Hz, 2H), 3.38 (s, 3H), 3.10 2.95 (m, 3H), 2.60 (t, J = 5.5 Hz, 2H), 2.54 (t, J = 6.6 Hz, 2H), 2.30-2.13 (m, 3H), 2.15-1.85(m, 5H); Mass (m/z): 393.2, 395.3 (M + H)$^+$. |
| 9. | 6-Chloro-8-{5-[1-(3-methyl-butyl)-piperidin-4-yl]-[1,3,4]oxadiazol-2-yl}-chroman-5-ylamine | $^1$H-NMR (CDCl$_3$): δ 7.67(s, 1H), 4.35 (s, 2H), 4.28 (t, J = 4.8 Hz, 2H), 3.05-2.90 (m, 3H), 2.54 (t, J = 6.5 Hz, 2H), 2.40-2.32 (m, 2H), 2.18-2.06 (m, 6H), 2.06-1.92 (m, 2H), 1.65-1.55 (m, 1H), 1.48-1.36(m, 2H), 0.92 (d, J = 6.5 Hz, 6H); Mass (m/z): 405.4, 407.4 (M + H)$^+$. |
| 10. | 6-Chloro-8-[5-(1-cyclobutylmethyl-piperidin-4-yl)-[1,3,4]oxadiazol-2-yl]-chroman-5-ylamine | $^1$H-NMR (DMSO-d$_6$): δ 7.48 (s, 1H), 5.79 (s, 2H), 4.14 (t, J = 4.8 Hz, 2H), 4.12 (s, 2H), 3.12-2.92 (m, 5H), 2.70-2.50 (m, 4H), 2.10-2.0 (m, H), 2.0-1.93 (m, 2H), 1.90-1.75 (m, 4H), 1.75-1.62 (m, 2H) Mass (m/z): 403.3, 405.3 (M + H)$^+$. |
| 11. | 6-Chloro-8-[5-(1-cyclopropylmethyl-piperidin-4-yl)-[1,3,4]oxadiazol-2-yl]-chroman-5-ylamine | $^1$H-NMR (DMSO-d6): δ 7.49 (s, 1H), 5.79 (s, 2H), 4.13 (t, J = 4.8 Hz, 2H), 4.10 (s, 2H), 3.30-3.15 (m, 2H), 3.15-3.05 (m, 3H), 2.70-2.55 (m, 4H), 2.18-2.07 (m, 2H), 2.0-1.80 (m, 4H), 1.0-.090 (m, 1H), 0.60-0.50 (m, 2H), 0.25-0.16 (m, 2H); Mass (m/z): 389.3, 391.4 (M + H)$^+$. |
| 12. | 6-Chloro-8-[5-(1-isopropyl-piperidin-4-yl)-[1,3,4]oxadiazol-2-yl]-chroman-5-ylamine | $^1$H-NMR (DMSO-d6): δ 7.49 (s, H), 5.80 (s, 2H), 4.22 (t, J = 4.8 Hz, 2H), 4.05 (s, 2H), 3.25-3.05 (m, 6H), 2.88-2.70 (m, 2H), 2.25-2.10 (m, 2H), 2.0-1.80 (m, 4H), 1.12 (d, J = 6.5 Hz, H); Mass (m/z): 377.3, 379.5 (M + H)$^+$. |
| 13. | 6-Chloro-8-{5-[1-(3-methoxy-propyl)-piperidin-4-yl]-[1,3,4]oxadiazol-2-yl}-chroman-5-ylamine | $^1$H-NMR (DMSO-d6): δ 7.48 (s, 1H), 5.79 (s, 2H), 4.13 (bs, 4H), 3.34 (t, J = 6.0 Hz, 2H), 3.30-3.22 (m, 1H), 3.21 (s, 3H), 3.20-3.0 (m, 4H), 2.70-2.60 (m, 2H), 2.60-2.50 (m, 2H), 2.15-2.03(m, 2H), 2.0-1.90 (m, 2H), 1.90-1.70 (m, 4H); Mass (m/z): 407.3, 409.2 (M + H)$^+$. |
| 14. | 6-Chloro-8-[5-(1-cyclobutyl-piperidin-4-yl)-[1,3,4]oxadiazol- | $^1$H-NMR (DMSO-d6): δ 7.48 (s, 1H), 4.14 (s, 2H), 4.13 (t, J = 4.8 Hz, 2H), 3.10-2.90 (m, 4H), 2.47 (t, J = 8.0 |

| | | |
|---|---|---|
| | 2-yl]-chroman-5-ylamine | Hz, 2H), 2.30-2.15 (m, 2H), 2.12-2.0 (m, 4H), 2.0-1.85 (m, 4H), 1.85-1.72 (m, 2H), 1.70-1.58 (m, 2H); Mass (m/z): 389.3, 391.4 (M + H)⁺. |
| 15. | 6-Chloro-8-[5-(1-cyclobutylmethyl-piperidin-4-yl)-[1,3,4]oxadiazol-2-yl]-2,3-dihydro-benzo[1,4]dioxin-5-ylamine | ¹H-NMR (DMSO-d6): δ 7.29 (s, 1H), 5.65 (s, 2H), 4.33(s, 4H), 4.11(s, 2H), 3.15-2.95(m, 3H), 2.70-2.55(m, 3H), 2.50-2.30(m, 2H), 2.10-2.0(m, 2H); Mass (m/z): 405.3, 407.4 (M + H)⁺. |
| 16. | 6-Chloro-8-[5-(1-cyclobutyl-piperidin-4-yl)-[1,3,4]oxadiazol-2-yl]-2,3-dihydro-benzo[1,4]dioxin-5-ylamine | ¹H-NMR (DMSO-d6): δ 7.29 (s, 1H), 5.65(s, 2H), 3.10-3.0(m, 1H), 3.0-2.85 (m, 3H), 2.30-2.12 (m, 2H), 2.10-1.95 (m, 4H), 1.95-1.70 (m, 4H), 1.70-1.53 (m, 2H); Mass (m/z): 391.4, 393.3 (M + H)⁺. |
| 17. | 6-Chloro-8-[5-(1-cyclopentyl-piperidin-4-yl)-[1,3,4]oxadiazol-2-yl]-chroman-5-ylamine tartarate salt | ¹H-NMR (DMSO-d6): δ 7.49 (s, 1H), 5.79 (s, 2H), 4.13 (t, J = 4.6 Hz, 2H), 4.0 (s, 2H), 3.25-3.08 (m, 3H), 3.05-2.90 (m, 1H), 2.68-2.53 (m, 2H), 2.47 (t, J = 7.8 Hz, 2H), 2.18-2.0 (m, 2H), 2.0-1.80 (m, 6H), 1.70-1.60 (m, 2H), 1.58-1.40 (m, 4H); Mass (m/z): 403.2, 405.7 (M + H)⁺. |
| 18. | 6-Chloro-8-[5-(2-piperidin-1-yl-ethyl)-[1,3,4]oxadiazol-2-yl]-chroman-5-ylamine | ¹H-NMR (CDCl₃): δ 7.69 (s, 1H), 4.35 (bs, 2H), 4.28 (t, J = 4.5 Hz, 2H), 3.20-3.05 (m, 2H), 2.90-2.80 (m, 2H), 2.80-2.70 (m, 2H), 2.65-2.50 (m, 4H), 2.20-2.10 (m, 2H), 2.10-1.95 (m, 1H), 1.60-1.48 (m, 1H), 1.50-1.40 (m, 2H); Mass (m/z): 363.2, 365.2 (M + H)⁺. |
| 19. | 4-[5-(5-Amino-6-chloro-chroman-8-yl)-[1,3,4]oxadiazol-2-yl]-[1,4']bipiperidinyl-1'-carboxylic acid ethyl ester | ¹H-NMR (DMSO-d6): δ 7.48 (s, 1H), 5.79 (s, 2H), 4.21 (s, 2H), 4.13 (t, J = 4.5 Hz, 2H), 4.10-3.95 (m, 4H), 3.20-3.05 (m, 4H), 2.90-2.72 (m, 4H), 2.70-2.60 (m, 2H), 2.20-2.08 (m, 2H), 2.0-1.90 (m, 2H), 1.90-1.75 (m, 4H), 1.50-1.35 (m, 2H), 1.16 (t, J = 7.0 Hz, 3H); Mass (m/z): 490.3, 492.3 (M + H)⁺. |
| 20. | 6-Chloro-8-[5-(3-piperidin-1-yl-propyl)-[1,3,4]oxadiazol-2-yl]-chroman-5-ylamine tartarate salt | ¹H-NMR (DMSO-d6): δ 7.48 (s, 1H), 5.79 (s, 2H), 4.13 (t, J = 4.8 Hz, 2H), 4.07 (s, 2H), 2.90 (t, J = 7.2 Hz, 2H), 2.85-2.70 (m, 6H), 2.47 (t, J = 6.5 Hz, 2H), 2.08-1.90 (m, 4H), 1.63-1.53 (m, 4H), 1.50-1.38 (m, 2H); Mass (m/z): 349.2, 351.4 (M + H)⁺. |
| 21. | 6-Chloro-8-[5-(1-cyclopentyl-piperidin-4-ylmethyl)-[1,3,4]oxadiazol-2-yl]-chroman-5-ylamine oxalate salt | ¹H-NMR (DMSO-d6): δ 7.47 (s, 1H), 5.80(s, 2H), 4.13(t, J = 4.8 Hz, 2H), 3.50-3.35 (m, 3H), 3.0-2.82 (m, 4H), 2.47 (t, J = 6.7 Hz, 2H), 2.10-1.88 (m, 7H), 1.70-1.40 (m, 8H); Mass (m/z): 417.3, 419.4 (M + H)⁺. |
| 22. | 6-Chloro-8-[5-(3-isopropyl-3-aza-bicyclo[3.1.0]hex-6-yl)-[1,3,4]oxadiazol-2-yl]-chroman-5-ylamine oxalate salt | ¹H-NMR (DMSO-d6): δ 7.47 (s, 1H), 5.79 (s, 2H), 4.12(t, J = 4.6 Hz, 2H), 3.75-3.55 (m, 2H), 3.40-3.20 (m, 3H), 2.58 (s, 1H), 2.46(t, J = 6.6 Hz, 2H), 2.42 (s, 2H), 2.0-1.90(m, 2H), 1.21 (d, J = 6.0 Hz, 6H); Mass (m/z): 375.2, 377.2 (M + H)⁺. |
| 23. | 6-Chloro-8-[5-(3-cyclobutylmethyl-3-aza-bicyclo[3.1.0]hex-6-yl)-[1,3,4]oxadiazol-2-yl]-chroman-5-ylamine oxalate salt | ¹H-NMR (DMSO-d6): δ 7.46 (s, 1H), 5.79(s, 2H), 4.12(t, J = 4.8 Hz), 3.60-3.45 (m, 2H), 3.20-1.90 (m, 4H), 2.55 (s, 1H), 2.46 (t, J = 6.9 Hz, 2H), 2.32 (s, 2H), 2.10-2.0(m, 2H), 2.0-1.90 (m, 3H), 1.90-1.80(m, 1H), 1.80-1.67(m, 3H); Mass (m/z): 400.9, 403.1 (M + H)⁺. |
| 24. | 6-Chloro-8-[5-(3-cyclopropylmethyl-3-aza-bicyclo[3.1.0]hex-6-yl)-[1,3,4]oxadiazol-2-yl]-chroman-5-ylamine | ¹H-NMR (CDCl₃): δ 7.65 (s, 1H), 4.33 (s, 2H), 4.27 (t, J = 4.9 Hz, 2H), 3.28 (d, J = 8.0 Hz, 2H), 2.70-2.63 (m, 1H), 2.53(t, J = 6.5 Hz, 2H), 2.50-2.42(m, 1H), 2.38-2.30(m, 2H), 2.17-2.07 (m, 4H), 0.90-0.80(m, 1H), 0.51-0.42(m, 2H), 0.15-0.06(m, 2H); Mass (m/z): 387.1, 389.1 (M + H)⁺. |
| 25. | 6-Chloro-8-{5-[1-(tetrahydro-pyran-4-yl)-piperidin-4-yl]-[1,3,4]oxadiazol-2-yl}-chroman-5-ylamine oxalate salt | ¹H-NMR (DMSO-d6): δ 7.49(s, 1H), 5.81 (s, 2H), 4.13 (t, J = 4.5 Hz, 2H), 4.0-3.90(m, 2H), 3.60-3.40 (m, 4H), 3.30(t, J = 11.2 Hz, 2H), 3.20-3.10 (m, 2H), 2.49(t, J = 6.7 Hz, 2H), 2.30-2.20(m, 2H), 2.10-1.88 (m, 6H), 1.70-1.58(m, 2H); Mass (m/z): 419.2, 421.2 (M + H)⁺ |
| 26. | 6-Chloro-8-{5-[1-(tetrahydro-pyran-4-ylmethyl)-piperidin-4-yl]-[1,3,4]oxadiazol-2-yl}-chroman-5-ylamine oxalate salt | ¹H-NMR (DMSO-d6): δ 7.49 (s, 1H), 5.81(s, 2H), 4.10-3.9(m, 2H), 3.90-3.80 (m, 2H), 3.27 (t, J = 11.9 Hz, 2H), 3.15-1.90 (m, 5H), 2.49 (t, J = 6.6 Hz, 2H), 2.30-2.20 (m, 2H), 2.18-1.90(m, 4H), 1.70-1.60(m, 2H), 1.30-1.10(m, 2H); Mass (m/z): 433.3, 435.2 (M + H)⁺. |
| 27. | 5-Chloro-7-[5-(1-cyclopropyl-piperidin-4-yl)-[1,3,4]oxadiazol-2-yl]-2,3-dihydro-benzofuran-4-ylamine oxalate salt | ¹H-NMR (DMSO-6): δ 7.49 (s, 1H), 6.02 (s, 2H), 4.68 (t, J = 8.8 Hz, 2H), 3.30-3.20 (m, 2H), 3.20-3.10 (m, 2H), 3.05 (t, J = 8.8 Hz, 2H), 2.90-2.75 (m, 2H), 2.30-2.20 (m, 1H), 2.18-2.07 (m, 2H), 1.90-1.77 (m, 2H), 0.70-0.58 (m, 4H); Mass (m/z): 361.1, 363.1 (M + H)⁺. |

| | | |
|---|---|---|
| 28. | 5-Chloro-7-[5-(1-cyclobutyl-piperidin-4-yl)-[1,3,4]oxadiazol-2-yl]-2,3-dihydro-benzofuran-4-ylamine oxalate salt | $^1$H-NMR (DMSO-d6): δ 7.49 (s, 1H), 6.0 (s, 2H), 4.68 (t, J = 8.8 Hz, 2H), 3.60-3.50 (m, 1H), 3.40-3.15 (m, 3H), 3.05 (t, J = 8.8 Hz, 2H), 2.90-2.70 (m, 2H), 2.30-2.10 (m, 6H), 2.05-1.90 (m, 2H), 1.80-1.60(m, 2H); Mass (m/z): 375.3, 377.0 (M + H)$^+$. |
| 29. | 6-Chloro-8-[5-(1-cyclopropyl-piperidin-4-yl)-[1,3,4]oxadiazol-2-yl]-2,3-dihydro-benzo[1,4]dioxin-5-ylamine oxalate salt | $^1$H-NMR (DMSO-d6): δ 7.29 (s, 1H), 5.65 (s, 2H), 4.33 (s, 4H), 3.35-3.25 (m, 2H), 3.25-3.13 (m, 1H), 2.93-2.82 (m, 2H), 2.37-2.28 (m, 1H), 2.20-2.10 (m, 2H), 1.90-1.80 (m, 2H), 0.70-0.60 (m, 4H); Mass (m/z): 377.1, 379.0 (M + H)$^+$. |
| 30. | 6-Chloro-8-{5-[1-(tetrahydro-pyran-4-yl)-piperidin-4-yl]-[1,3,4]oxadiazol-2-yl}-2,3-dihydro-benzo[1,4]dioxin-5-ylamine oxalate salt | $^1$H-NMR (DMSO-d6): δ 7.30 (s, 1H), 5.66 (s, 2H), 4.33 (s, 4H), 4.0-3.90 (m, 2H), 3.40-3.20(m, 6H), 3.10-3.0(m, 2H), 2.30-2.20 (m, 2H), 2.10-1.92 (m, 2H), 1.92-1.85 (m, 2H), 1.70-1.55 (m, 2H); Mass (m/z): 421.1, 423.2 (M + H)$^+$. |
| 31. | 6-Chloro-8-{5-[1-(3-methoxy-propyl)-piperidin-4-yl]-[1,3,4]oxadiazol-2-yl}-2,3-dihydro-benzo[1,4]dioxin-5-ylamine oxalate salt | $^1$H-NMR (DMSO-d6): δ 7.30 (s, 1H), 5.68 (s, 2H), 4.33 (s, 4H), 3.50-3.40 (m, 2H), 3.37 (t, J = 5.8 Hz, 2H), 3.38-3.28 (m, 1H), 3.23 (s, 3H), 3.10-2.95 (m, 4H), 2.30-2.20 (m, 2H), 2.10-1.92 (m, 2H), 1.90-1.82 (m, 2H); Mass (m/z): 409.1, 411.0 (M + H)$^+$. |
| 32. | 6-Chloro-8-{5-[1-(tetrahydro-pyran-4-ylmethyl)-piperidin-4-yl]-[1,3,4]oxadiazol-2-yl}-2,3-dihydro-benzo[1,4]dioxin-5-ylamine oxalate salt | $^1$H-NMR (DMSO-d6): δ 7.29 (s, 1H), 5.68 (s, 2H), 4.33 (s, 4H), 3.90-3.80 (m, 2H), 3.50-3.30 (m, 2H), 3.29 (t, J = 11.4 Hz, 2H), 3.08-2.90 (m, 1H), 2.90-2.80 (m, 2H), 2.28-2.16(m, 2H), 2.12-1.95 (m, 3H), 1.70-1.60 (m, 2H), 1.28-1.10 (m, 2H); Mass (m/z): 435.2, 437.3 (M + H)$^+$. |
| 33. | 5-Chloro-7-{5-[1-(tetrahydro-pyran-4-ylmethyl)-piperidin-4-yl]-[1,3,4]oxadiazol-2-yl}-2,3-dihydro-benzofuran-4-ylamine oxalate | $^1$H-NMR (CDCl$_3$): δ 7.49 (s, 1H), 6.03(s, 2H), 4.68(t, J = 8.8 Hz, 2H), 3.90-3.80 (m, 2H), 3.40-3.20 (m, 5H), 3.05 (t, J = 8.8 Hz, 2H), 3.0-2.90 (m, 2H), 2.90-2.80(m, 2H), 2.25-2.15 (m, 2H), 2.10-1.92 (m, 3H), 1.70-1.60 (m, 2H), 1.30-1.13 (m, 2H); Mass (m/z): 419.1, 421.2 (M + H)$^+$. |
| 34. | 4-[5-(4-Amino-5-chloro-2,3-dihydro-benzofuran-7-yl)-[1,3,4]oxadiazol-2-yl]-[1,4']bipiperidinyl-1'-carboxylic acid ethyl ester oxalate | $^1$H-NMR (DMSO-d6): δ 7.49 (s, 1H), 6.03 (s, 2H), 4.68(t, J = 8.7 Hz, 2H), 4.15-4.00 (m, 4H), 3.40-3.15(m, 4H), 3.05(t, J = 8.7 Hz, 2H), 3.05-2.92 (m, 2H), 2.90-2.70(m, 2H), 2.30-2.20 (m, 2H), 2.10-1.90(m, 4H), 1.60-1.42(m, 2H), 1.17(t, J = 7.0 Hz, 3H); Mass (m/z): 476.1, 478.2 (M + H)$^+$. |
| 35. | 3-[5-(1-Cyclobutylmethyl-piperidin-4-yl)-[1,3,4]oxadiazol-2-yl]-1-isopropyl-1H-indazole | $^1$H-NMR (DMSO-d6): δ 8.17 (d, J = 8.1 Hz, 1H), 7.90(d, J = 8.56 Hz, 1H), 7.54(t, J = 7.5 Hz, 1H), 7.38(t, J = 7.6 Hz, 1H), 5.2-5.13(m, 1H), 4.12 (s, 2H), 3.3-3.2(m, 2H), 3.12-3.02(m, 2H), 2.7-2.62(m, 2H), 2.6-2.55(m, 1H), 2.48-2.43(m, 1H), 2.2-2.1 (m, 2H), 2.1-2.0 (m, 2H), 1.98-1.87(m, 2H), 1.86-1.72 (m, 1H), 1.71-1.63 (m, 2H), 1.54(d, J = 6.5 Hz, 6H); Mass (m/z): 380 (M + H)$^+$. |
| 36. | 1-Isopropyl-3-{5-[1-(2-methoxy-ethyl)-piperidin-4-yl]-[1,3,4]oxadiazol-2-yl}-1H-indazole | $^1$H-NMR (CDCl$_3$): δ 8.35(d, J = 8.1 HZ, 1H), 7.53 (d, J = 8.3 Hz, 1H), 7.47 (t, J = 6.9 Hz, 1H), 7.33(t, J = 7.3 Hz, 1H), 5.0-4.91(m, 1H), 3.55 (t, J = 5.3 Hz, 2H), 3.38(s, 3H), 3.12-3.1(m, 3H), 2.63(t, J = 5.2 Hz, 2H), 2.25-2.12 (m, 6H), 1.66 (d, J = 6.6 Hz, 6H); Mass (m/z): 370 (M + H)$^+$. |
| 37. | 3-[5-(1-Cyclobutyl-piperidin-4-yl)-[1,3,4]oxadiazol-2-yl]-1-isopropyl-1H-indazole | $^1$H-NMR (CDCl$_3$): δ 8.33 (d, J = 8.2 Hz, 1H), 7.52 (d, J = 8.5 HZ, 1H), 7.47(t, J = 7.9 Hz, 1H), 7.33(t, J = 7.5 Hz, 1H), 5.0-4.93(m, 1H), 3.15-3.08(m, 1H), 2.98-2.96(m, 2H), 2.8-2.7(m, 1H), 2.3-2.2(m, 2H), 2.16-2.05 (m, 5H), 2.0-1.9 (m, 3H), 1.75-1.69 (m, 2H), 1.67(d, J = 6.7 Hz, 6H); Mass (m/z): 366.4 (M + H)$^+$. |
| 38. | 1-Isopropyl-3-[5-(1-isopropyl-piperidin-4-yl)-[1,3,4]oxadiazol-2-yl]-1H-indazole | $^1$H-NMR (CDCl$_3$): δ 8.35(d, J = 8.16 Hz, 1H), 7.53 (d, J = 8.48 Hz, 1H), 7.47 9t, J = 7.97 Hz, 1H), 7.33(t, J = 7.48 Hz, 1H), 5.00-4.93(m, 1H), 3.06-2.96 (m, 3H), 2.8-2.75(m, 2H), 2.35-2.30(m, 2H), 2.25-2.17 (m, 2H), 2.12-2.03(m, 2H), 1.65(d, J = 6.8 Hz, 6H), 1.87(d, J = 6.5 Hz, 6H); Mass (m/z): 354 (M + H)$^+$. |
| 39. | 3-[5-(1-Cyclopropylmethyl-piperidin-4-yl)-[1,3,4]oxadiazol-2-yl]-1-isopropyl-1H-indazole | $^1$H-NMR (CDCl$_3$): δ8.35 (d, J = 8.1 Hz, 1H), 7.53(d, J = 8.4 Hz, 1H), 7.47(t, J = 6.7 Hz, 1H), 7.33(t, J = 7.46 Hz, 1H), 5.03-4.95(m, 1H), 3.18-3.15 (m, 2H), 3.15-3.07(m, 1H), 2.31(d, J = 6.5 Hz, 2H), 2.22-2.1(m, 6H), 1.67(d, J = 6.68 Hz, 6H), 0.98-0.91 (m, 1H), 0.57-0.52 (m, 2H), 0.14-0.11(m, 2H); Mass (m/z): 366 (M + H)$^+$. |
| 40. | 1-Isopropyl-3-{5-[1-(3-methyl-butyl)-piperidin-4-yl]- | $^1$H-NMR (CDCl$_3$): δ 8.35 (d, J = 8.1 Hz, 1H), 7.53(d, J = 8.46 Hz, 1H), 7.47(t, J = 6.91 Hz, 1H), 7.33(t, J = 7.6 Hz, |

-continued

| | |
|---|---|
| [1,3,4]oxadiazol-2-yl}-1H-indazole | 1H), 5.0-4.93(m, 1H), 3.10-2.98(m, 3H), 1.67(d, J = 6.68 Hz, 6H), 1.45-1.40(m, 2H), 0.92(d, J = 6.57 Hz, 6H); Mass (m/z): 382 (M + H)$^+$. |
| 41. 3-[5-(1-Cyclopropyl-piperidin-4-yl)-[1,3,4]oxadiazol-2-yl]-1-isopropyl-1H-indazole | $^1$H-NMR (CDCl$_3$): δ 8.35(d, J = 8.17 Hz, 1H), 7.53(d, J = 8.48 Hz, 1H), 7.47(t, J = 6.96 Hz, 1H), 7.33(t, J = 7.47 Hz, 1H), 5.0-4.93(m, 1H), 3.16-3.05(m, 3H), 2.37 (t, J = 11.3 Hz, 2H), 2.19-2.16(m, 2H), 2.07-1.98(m, 2H), 1.67(d, J = 6.6 Hz, 6H), 1.63-1.57 (m, 1H), 051-046 (m. 4H); Mass (m/z): 352 (M + H)$^+$. |
| 42. 3-[5-(1-Cyclopentyl-piperidin-4-yl)-[1,3,4]oxadiazol-2-yl]-1-isopropyl-1H-indazole | $^1$H-NMR (CDCl$_3$): δ 8.35 (d, J = 9.39 Hz, 1H), 7.53(d, J = 8.49 Hz, 1H), 7.47(t, J = 8.0 Hz, 1H), 7.33 (t, J = 7.43 Hz), 5.0-4.93 (m, 1H), 3.15-3.05(m, 3H), 2.6-2.53(m, 1H), 2.22-2.10(m, 6H), 1.98-1.90(m, 2H), 1.74-1.69(m, 2H), 1.67(d, J = 6.69 Hz, 6H), 1.60-1.55 (m, 2H), 1.45-1.38 (m, 2H); Mass (m/z): 380 (M + H)$^+$. |
| 43. 1-Isopropyl-3-{5-[3-(3-methoxy-propyl)-3-aza-bicyclo[3.1.0]hex-6-yl]-[1,3,4]oxadiazol-2-yl}-1H-indazole oxalate salt | $^1$H-NMR (DMSO-d$_6$): δ 8.15(d, J = 8.2 Hz, 1H), 7.89(d, J = 8.1 Hz, 1H), 7.53 (t, J = 7.5 Hz, 1H), 7.36 (t, J = 7.4 Hz, 1H), 5.20-5.10 (m, 1H), 3.60-3.50 (m, 2H), 3.36 (t, J = 5.8 Hz, 2H), 3.23 (s, 3H), 3.10-3.0 (m, 2H), 3.0-2.86 (m, 2H), 2.68 (s, 1H), 2.43 (s, 2H), 1.85-1.72 (m, 2H), 1.53 (d, J = 6.3 Hz, 6H); Mass (m/z): 382.3 (M + H)$^+$. |
| 44. 3-[5-(3-Cyclobutyl-3-aza-bicyclo[3.1.0]hex-6-yl)-[1,3,4]oxadiazol-2-yl]-1-isopropyl-1H-indazole oxalate salt | $^1$H-NMR (CDCl$_3$): δ 8.34 (d, J = 8.1 Hz, 1H), 7.52 (d, J = 8.4 Hz, 1H), 7.46 (t, J = 8.0 Hz, 1H), 7.29 (t, J = 7.3 Hz, 1H), 5.0-4.90 (m, 1H), 3.11 (d, J = 9.0 Hz, 2H), 3.10-3.0 (m, 1H), 2.73 (s, 1H), 2.41 (d, J = 8.3 Hz, 2H), 2.2 (s, 2H), 2.06-1.95 (m, 2H), 1.95-1.80 (m, 2H), 1.75-1.65 (m, 2H), 1.67 (d, J = 6.7 Hz, 6H); Mass (m/z): 364.2 (M + H)$^+$. |
| 45. 3-[5-(3-Cyclobutylmethyl-3-aza-bicyclo[3.1.0]hex-6-yl)-[1,3,4]oxadiazol-2-yl]-1-isopropyl-1H-indazole oxalate salt | $^1$H-NMR (DMSO-d$_6$): δ 8.14 (d, J = 8.1 Hz, 1H), 7.89 (d, J = 8.4 Hz, 1H), 7.53 (t, J = 7.4 Hz, 1H), 7.36 (t, J = 7.6 Hz, 1H), 5.20-5.10 (m, 1H), 3.55-3.40 (m, 2H), 3.10-3.0 (m, 2H), 2.95-2.85 (m, 2H), 2.67 (s, 1H), 2.60-2.50 (m, 1H), 2.41 (s, 2H), 2.10-1.98 (m, 2H), 1.90-1.80 (m, 1H), 1.85-1.65 (m, 3H), 1.52 (d, J = 6.0 Hz, 6H); Mass (m/z): 378.2 (M + H)$^+$. |
| 46. 3-[5-(3-Cyclopropylmethyl-3-aza-bicyclo[3.1.0]hex-6-yl)-[1,3,4]oxadiazol-2-yl]-1-isopropyl-1H-indazole oxalate salt | $^1$H-NMR (CDCl$_3$): δ 8.34 (d, J = 8.1 Hz, 1H), 7.52 (d, J = 8.3 Hz, 1H), 7.46 (t, J = 8.1 Hz, 1H), 7.32 (t, J = 7.5 Hz, 1H), 5.0-4.90 (m, 1H), 3.30 (d, J = 8.9 Hz, 2H), 2.77 (s, 1H), 2.48 (d, J = 8.6 Hz, 2H), 2.20 (s, 2H), 1.67 (d, J = 6.0 Hz, 6H), 0.90-0.80 (m, 1H), 0.50-0.40 (m, 2H), 0.18-0.08 (m, 2H); Mass (m/z): 364.1 (M + H)$^+$. |
| 47. 1-Isopropyl-3-{5-[1-(tetrahydro-pyran-4-ylmethyl)-piperidin-4-yl]-[1,3,4]oxadiazol-2-yl}-1H-indazole oxalate salt | $^1$H-NMR (DMSO-d$_6$): δ 8.18 (d, J = 8.03 Hz, 1H), 7.90 (d, J = 8.4 Hz, 1H), 7.54 (t, J = 8.0 Hz, 1H), 7.38 (t, J = 7.3 Hz, 1H), 5.20-5.14 (m, 1H), 3.90-3.80 (m, 2H), 3.37-3.27 (m, 5H), 2.98-2.89 (m, 2H), 2.88-2.77 (m, 2H), 2.29-2.23 (m, 2H), 2.27-2.03 (m, 3H), 1.67-1.63 (m, 2H), 1.54 (d, J = 6.4 Hz, 6H), 1.22-1.15 (m, 2H); Mass (m/z): 410.1 (M + H)$^+$. |
| 48. 1-Isopropyl-3-{5-[1-(tetrahydro-pyran-4-yl)-piperidin-4-yl]-[1,3,4]oxadiazol-2-yl}-1H-indazole oxalate salt | $^1$H-NMR (DMSO-d$_6$): δ 8.18 (d, J = 8.1 Hz, 1H), 7.9 (d, J = 8.5 Hz, 1H), 7.54 (t, J = 7.1 Hz, 1H), 7.38 (t, J = 7.3 Hz, 1H), 5.20-5.14 (m, 1H), 4.0-3.90 (m, 2H), 3.47-3.40 (m, 3H), 3.40-3.20 (m, 3H), 3.15-3.01 (m, 2H), 2.38-2.25 (m, 2H), 2.11-2.06 (m, 2H), 1.95-1.86 (m, 2H), 1.66-1.60 (m, 2H), 1.54 (d, J = 6.5 Hz, 6H); Mass (m/z): 396.2 (M + H)$^+$. |
| 49. 1-Isopropyl-3-[5-(2-piperidin-1-yl-ethyl)-[1,3,4]oxadiazol-2-yl]-1H-indazole oxalate | $^1$H-NMR (DMSO-d6): δ 8.19(d, J = 8.1 Hz, 1H), 7.91 (d, J = 8.5 Hz, 1H), 7.55(t, J = 7.5 Hz, 1H), 7.38(t, J = 7.6 Hz, 1H), 5.21-5.14(m, 1H), 3.49-3.41(m, 4H), 3.15-3.06(m, 4H), 1.76-1.64(m, 4H), 1.54(d, J = 6.59 Hz, 6H), 1.54-1.45(m, 2H); Mass (m/z): 340(M + H)$^+$. |

Biological Assays

Example 50

Determination of EC50 Values for 5-HT$_4$ Receptor

A stable CHO cell line expressing recombinant human 5-HT$_4$ receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50%.

| Example Number | EC50 (nM) |
|---|---|
| 1. | 28.5 |
| 2. | 47 |
| 3. | 27.5 |
| 4. | 38 |
| 5. | 18 |
| 6. | 4.2 |
| 7. | 7 |
| 8. | 15.6 |
| 9. | 2.4 |
| 10. | 5.7 |
| 11. | 10.2 |
| 12. | 15.3 |
| 13. | 20.4 |
| 14. | 1.3 |
| 15. | 6.2 |
| 16. | 13.3 |
| 17. | 2.3 |
| 18. | 53 |
| 19. | 6.8 |
| 20. | 104 |
| 21. | 71.2 |
| 22. | 48 |
| 23. | 20 |
| 24. | 25 |
| 25. | 5.7 |
| 26. | 18 |
| 27. | 60 |
| 28. | 10 |
| 29. | 21.5 |
| 30. | 7.3 |
| 31. | 16.9 |
| 33. | 21 |
| 34. | 5 |
| 35. | 169 |
| 36. | 143 |
| 37. | 127 |
| 38. | 23 |
| 39. | 66 |

-continued

| Example Number | EC50 (nM) |
|---|---|
| 40. | 116 |
| 41. | 199 |
| 42. | 72 |
| 47. | 84.5 |
| 48. | 54 |
| 49. | 181 |

Example 51

Rodent Pharmacokinetic Study

Male Wister rats (225±25 grams) were used as an experimental animal. Three to five animals were housed in each cage. Two days prior to dosing day, male wister rats (225-250 grams) were anesthetized with isoflurane for surgical placement of jugular vein catheter. Animals were fasted over night before oral dosing (p.o) and food pellets were allowed 2 hours post dosing, whereas intravenous dosing food and water were provided as ad libitum. Three rats were dosed with compounds of formula (I) (10 mg/kg) orally and intravenously (05 mg/kg).

At each time point blood was collected through jugular vein and immediately replenish with an equivalent volume of normal saline from freely moving rats. Collected blood was transferred into a labeled eppendr off containing 10 μL of heparin as anticoagulant. Typically blood samples were collected as following time points: Pre dose, 0.08 (only i.v.), 0.25, 0.5, 1, 2, 4, 6, 8, and 24 hours post dose (n=3). Blood was centrifuged at 4000 rpm for 10 minutes. Plasma was prepared and stored frozen at −20° C. until analysis. The concentrations of the compounds of formula (I) were quantified in plasma by qualified LC-MS/MS method using suitable extraction technique. The compounds of formula (I) were quantified in the calibration range around 2-2000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using standard non-compartmental model by using WinNonLin 5.0.1 or Phoenix WinNonlin 6.2 version Software package.

| Example Number | Strain/ Gender | Dose (mg/kg) | Vehicle | Route of administration | $C_{max}$ (ng/mL) | $T_{max}$ (h) | $AUC_t$ (ng · hr/mL) | $T_{1/2}$ (h) | Bioavailability (%) |
|---|---|---|---|---|---|---|---|---|---|
| 3. | Wistar/Male | 10 | Reagent grade water | oral (gavage) | 360 ± 46 | 0.42 ± 0.12 | 709 ± 120 | 1.27 ± 0.23 | 34 ± 13 |
| | Wistar/Male | 5 | Sterile water for injection | intravenous (bolus) | 811 ± 181 | 0.08 ± 0.00 | 1117 ± 285 | 1.66 ± 0.06 | |
| 8. | Wistar/Male | 10 | Reagent grade water | oral (gavage) | 918 ± 46 | 0.33 ± 0.14 | 1765 ± 89 | 1.01 ± 0.08 | 72 ± 22 |
| | Wistar/Male | 5 | Sterile water for injection | intravenous (bolus) | 1284 ± 239 | 0.08 ± 0.00 | 1324 ± 527 | 1.03 ± 0.14 | |
| 9. | Wistar/Male | 10 | Reagent grade water | oral (gavage) | 412 ± 177 | 0.67 ± 0.24 | 1214 ± 941 | 1.49 ± 0.64 | 66 ± 21 |
| | Wistar/Male | 5 | Sterile water for injection | intravenous (bolus) | 792 ± 111 | 0.08 ± 0.00 | 836 ± 374 | 1.38 ± 0.66 | |

| Example Number | Strain/ Gender | Dose (mg/kg) | Vehicle | Route of administration | $C_{max}$ (ng/mL) | $T_{max}$ (h) | $AUC_t$ (ng · hr/mL) | $T_{1/2}$ (h) | Bio-availability (%) |
|---|---|---|---|---|---|---|---|---|---|
| 14. | Wistar/ Male | 10 | Reagent grade water | oral (gavage) | 513 ± 125 | 0.25 ± 0.00 | 645 ± 136 | 0.96 ± 0.11 | 42 ± 10 |
|  | Wistar/ Male | 5 | Sterile water for injection | intravenous (bolus) | 783 ± 124 | 0.08 ± 0.00 | 773 ± 45 | 1.22 ± 0.26 |  |
| 19. | Wistar/ Male | 10 | Reagent grade water | oral (gavage) | 1758 ± 264 | 0.50 ± 0.00 | 4814 ± 30 | 1.48 ± 0.18 | 101 ± 1 |
|  | Wistar/ Male | 5 | Sterile water for injection | intravenous (bolus) | 1858 ± 115 | 0.08 ± 0.00 | 2373 ± 90 | 2.21 ± 0.23 |  |
| 20. | Wistar/ Male | 10 | Reagent grade water | oral (gavage) | 602 ± 35 | 0.25 ± 0.00 | 790 ± 153 | 1.03 ± 0.02 | 46 ± 9 |
|  | Wistar/ Male | 5 | Sterile water for injection | intravenous (bolus) | 976 ± 305 | 0.08 ± 0.00 | 867 ± 173 | 0.80 ± 0.06 |  |
| 21. | Wistar/ Male | 10 | Reagent grade water | oral (gavage) | 553 ± 53 | 0.42 ± 0.12 | 1490 ± 72 | 1.57 ± 0.11 | 85 ± 4 |
|  | Wistar/ Male | 5 | Sterile water for injection | intravenous (bolus) | 750 ± 14 | 0.08 ± 0.00 | 876 ± 65 | 1.79 ± 0.43 |  |
| 37. | Wistar/ Male | 10 | Reagent grade water | oral (gavage) | 248 ± 43 | 0.33 ± 0.12 | 392 ± 103 | 2.03 ± 0.44 | 22 ± 3 |
|  | Wistar/ Male | 5 | Sterile water for injection | intravenous (bolus) | 612 ± 59 | 0.08 ± 0.00 | 878 ± 209 | 1.68 ± 0.30 |  |
| 39. | Wistar/ Male | 10 | Reagent grade water | oral (gavage) | 179 ± 80 | 0.42 ± 0.12 | 394 ± 174 | 1.38 ± 0.07 | 19 ± 8 |
|  | Wistar/ Male | 5 | Sterile water for injection | intravenous (bolus) | 865 ± 122 | 0.08 ± 0.00 | 1060 ± 163 | 1.65 ± 0.47 |  |
| 47. | Wistar/ Male | 10 | Reagent grade water | oral (gavage) | 587 ± 340 | 0.50 ± 0.43 | 1323 ± 364 | 1.84 ± 0.39 | 66 ± 18 |
|  | Wistar/ Male | 5 | Sterile water for injection | intravenous (bolus) | 815 ± 125 | 0.08 ± 0.00 | 1004 ± 109 | 1.44 ± 0.22 |  |
| 48. | Wistar/ Male | 10 | Reagent grade water | oral (gavage) | 521 ± 111 | 0.25 ± 0.00 | 695 ± 119 | 1.21 ± 0.04 | 40 ± 7 |
|  | Wistar/ Male | 5 | Sterile water for injection | intravenous (bolus) | 711 ± 163 | 0.08 ± 0.00 | 863 ± 95 | 1.66 ± 0.33 |  |

Example 52

Rodent Brain Penetration Study

Male Wister rats (225±25 grams) were used as an experimental animal. Three animals were housed in each cage. Animals were given water and food ad libitum throughout the experiment, and maintained on a 12 hours light/dark cycle.

Brain penetration was determined in discrete manner in rats. One day prior to dosing day, male wistar rats (225-250 grams) were acclimatized. After acclimatization the rats were grouped according to the weight in each group, 3 animals were kept in individual cage and allowed free access to food and water. At each time point (0.50, 1, and 2 hours) n=3 animals were used.

The compounds of formula (I) was suitably preformulated and administered orally at (free base equivalent) 10 mg/kg. Blood samples were removed via, cardiac puncture by using isoflurane anesthesia the animals were sacrificed to collect brain tissue. Plasma was separated and Brain samples were homogenized and stored frozen at −20° C. until analysis. The concentrations of the NCE compound in plasma and Brain were determined using LC-MS/MS method.

The compounds of formula (I) were quantified in plasma and brain homogenate by qualified LC-MS/MS method using suitable extraction technique. The compounds of formula (I) were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$).

| Example Number | Strain/ Gender | Dose (mg/kg) | Vehicle | Route of administration | Single dose Brain Penetration ($C_b/C_p$) |
|---|---|---|---|---|---|
| 3. | Wistar/ Male | 10 | Reagent grade water | oral (gavage) | 3.88 ± 0.26 |
|  | Wistar/ Male | 5 | Sterile water for injection | intravenous (bolus) |  |
| 8. | Wistar/ Male | 10 | Reagent grade water | oral (gavage) | 0.56 ± 0.08 |
|  | Wistar/ Male | 5 | Sterile water for injection | intravenous (bolus) |  |
| 14. | Wistar/ Male | 10 | Reagent grade water | oral (gavage) | 2.24 ± 0.09 |
|  | Wistar/ Male | 5 | Sterile water for injection | intravenous (bolus) |  |
| 20. | Wistar/ Male | 10 | Reagent grade water | oral (gavage) | 0.50 ± 0.07 |
|  | Wistar/ Male | 5 | Sterile water for injection | intravenous (bolus) |  |
| 21. | Wistar/ Male | 10 | Reagent grade water | oral (gavage) | 0.62 ± 0.05 |
|  | Wistar/ Male | 5 | Sterile water for injection | intravenous (bolus) |  |
| 37. | Wistar/ Male | 10 | Reagent grade water | oral (gavage) | 5.68 ± 1.74 |
|  | Wistar/ Male | 5 | Sterile water for injection | intravenous (bolus) |  |
| 39. | Wistar/ Male | 10 | Reagent grade water | oral (gavage) | 4.69 ± 0.69 |
|  | Wistar/ Male | 5 | Sterile water for injection | intravenous (bolus) |  |
| 47. | Wistar/ Male | 10 | Reagent grade water | oral (gavage) | 3.15 ± 0.57 |
|  | Wistar/ Male | 5 | Sterile water for injection | intravenous (bolus) |  |
| 48. | Wistar/ Male | 10 | Reagent grade water | oral (gavage) | 2.55 ± 0.32 |
|  | Wistar/ Male | 5 | Sterile water for injection | intravenous (bolus) |  |

Example 53

Object Recognition Task Model

The cognition enhancing properties of compounds of this invention were estimated by using this model.

Male Wister rats (230-280 grams) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cms from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed. T1 is the total time spent exploring the familiar objects (a1+a2). T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

| Example Number | Dose mg/kg, p.o. | Exploration time mean ± S.E.M (sec) | | Inference |
|---|---|---|---|---|
| | | Familiar object | Novel object | |
| 1. | 3 mg/kg, p.o. | 5.08 ± 0.1 | 13.80 ± 2.20 | Active |
| 3. | 3 mg/kg, p.o. | 6.88 ± 0.97 | 12.86 ± 1.32 | Active |
| 8. | 3 mg/kg, p.o. | 10.45 ± 1.162 | 17.59 ± 2.95 | Active |
| 9. | 3 mg/kg, p.o. | 11.21 ± 2.18 | 16.47 ± 1.18 | Active |
| 14. | 1 mg/kg, p.o. | 5.06 ± 1.32 | 12.68 ± 1.14 | Active |
| 15. | 1 mg/kg, p.o. | 12.03 ± 1.73 | 19.14 ± 3.02 | Active |
| 16. | 10 mg/kg, p.o. | 8.03 ± 1.58 | 13.94 ± 1.76 | Active |
| 19. | 10 mg/kg, p.o. | 7.19 ± 0.65 | 13.21 ± 2.1 | Active |
| 20. | 3 mg/kg, p.o. | 4.69 ± 0.79 | 11.04 ± 1.33 | Active |
| 25. | 3 mg/kg, p.o. | 5.93 ± 0.87 | 14.70 ± 2.34 | Active |
| 26. | 3 mg/kg, p.o. | 7.12 ± 1.44 | 14.42 ± 2.22 | Active |
| 37. | 1 mg/kg, p.o. | 5.84 ± 1.11 | 20.19 ± 2.67 | Active |

Example 54

Radial Arm Maze

The cognition enhancing properties of compounds of this invention were estimated by using this model.

Radial arm maze consists of a central hub of 45 cm diameter. Each arm was of dimension 42.5×15×24 cm. The maze was elevated to a height of 1 m above the ground. The animals were place on a restricted diet until they reached approximately 85% of their free feeding weight. During this diet restriction period animals were habituated to the novel feed (pellets). Once the rats reached approximately 85% of their free feeding weight rats were habituated to the maze on the $1^{st}$ & $2^{nd}$ day. The animals that did not eat the pellets were rejected from the study. Animals were randomized on day 2. On the subsequent days the treatment was given as per the allotment. Each animal was introduced into the maze individually for a period of 10 minutes. The arms were baited only once and the animal had to learn the rule that repeated arm entries would not be rewarded. The trial ended once the rat had visited 16 arms or 10 minutes were over or all the pellets were eaten. The arm entries were recorded using the software. Once the trial was over the rat was removed and the maze was cleaned using soap water.

| Example Number | Reversal of Scopolamine Induced amnesia - Effective dose range |
|---|---|
| 3. | 1-3 mg/kg, p.o. |
| 14. | 1-10 mg/kg, p.o. |

We claim:
1. A compound of the general formula (I):

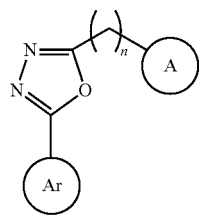

(I)

wherein,

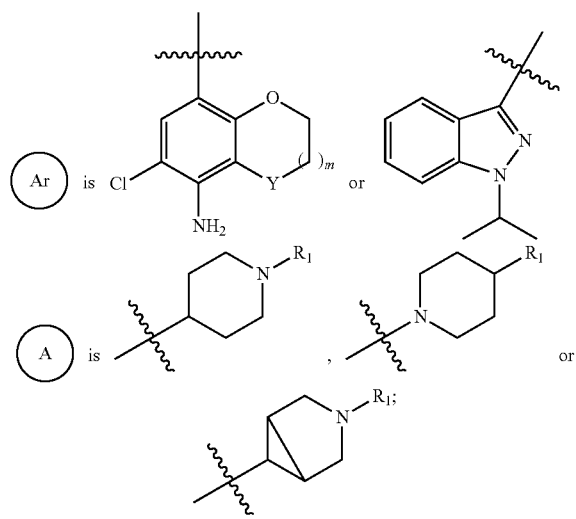

 is point of attachment;
R$_1$ is alkyl, R$_3$—O—R$_3$ or

R$_2$ is cycloalkyl, pyrrolidinyl, piperidinyl, piperazinyl, morpholinyl or tetrahydropyranyl, and optionally substituted with hydrogen, alkyl or —CO—OR$_3$;
R$_3$ is alkyl;
"Y" is C or O;
"m" is an integer ranging from 0 to 1; with proviso when m is 0 then R$_1$ is cycloalkyl pyrrolidinyl, piperidinyl, piperazinyl, morpholinyl or tetrahydropyranyl;
"n" is an integer ranging from 0 to 2;
"p" is an integer ranging from 0 to 1; or a pharmaceutically acceptable salt thereof.

2. The compound as claimed in claim 1, which is selected from the group consisting of:
6-Chloro-8-[5-(1-cyclopropyl-piperidin-4-yl)-[1,3,4]oxadiazol-2-yl]-chroman-5-ylamine hemi fumarate;
6-Chloro-8-[5-(1-cyclobutyl piperdin-4-ylmethyl)-[1,3,4] oxadiazol-2-yl]-chroman-5-yl amine L(+)-tartarate salt;
6-Chloro-8-[5-(1-cyclobutyl piperdin-4-yl methyl)-[1,3,4] oxadiazol-2-yl]-chroman-5-yl amine;
1-Isopropyl-3-{5-[1-(3-methoxy propyl)piperidin-4-yl]-[1,3,4]oxadiazol-2-yl}-1H-indazole oxalate salt;
3-[5-(1-Cyclobutyl-piperidin-4-yl methyl)-[1,3,4]oxadiazol-2-yl]-1-isopropyl-1H-indazole L(+)-tartarate salt;
6-Chloro-8-[5-(3-cyclobutyl-3-aza bicyclo[3.1.0]hex-6-yl)-[1,3,4]oxadiazol-2-yl]chroman-5-ylamine oxalate salt;
4-[5-(8-Amino-7-chloro-2,3-dihydro benzo[1,4]dioxan-5-yl)-[1,3,4]oxadiazol-2-yl]-[1,4]bipiperidinyl-1'-carboxylic acid ethyl ester oxalate salt;
5-Chloro-7-{5-[1-(tetrahydro pyran-4-yl) piperidin-4-yl]-[1,3,4]oxadiazol-2-yl}-2,3-dihydro benzofuran-4-yl amine oxalate salt;
6-Chloro-8-{5-[1-(2-methoxy-ethyl)-piperidin-4-yl]-[1,3,4]oxadiazol-2-yl}-chroman-5-ylamine;
6-Chloro-8-{5-[1-(3-methyl-butyl)-piperidin-4-yl]-[1,3,4]oxadiazol-2-yl}-chroman-5-ylamine;
6-Chloro-8-[5-(1-cyclobutylmethyl-piperidin-4-yl)-[1,3,4]oxadiazol-2-yl]-chroman-5-ylamine;
6-Chloro-8-[5-(1-cyclopropylmethyl-piperidin-4-yl)-[1,3,4]oxadiazol-2-yl]-chroman-5-ylamine;
6-Chloro-8-[5-(1-isopropyl-piperidin-4-yl)-[1,3,4]oxadiazol-2-yl]-chroman-5-ylamine;
6-Chloro-8-{5-[1-(3-methoxy-propyl)-piperidin-4-yl]-[1,3,4]oxadiazol-2-yl}-chroman-5-ylamine;
6-Chloro-8-[5-(1-cyclobutyl-piperidin-4-yl)-[1,3,4]oxadiazol-2-yl]-chroman-5-ylamine;
6-Chloro-8-[5-(1-cyclobutylmethyl-piperidin-4-yl)-[1,3,4]oxadiazol-2-yl]-2,3-dihydro-benzo[1,4]dioxin-5-ylamine;
6-Chloro-8-[5-(1-cyclobutyl-piperidin-4-yl)-[1,3,4]oxadiazol-2-yl]-2,3-dihydro-benzo[1,4]dioxin-5-ylamine;
6-Chloro-8-[5-(1-cyclopentyl-piperidin-4-yl)-[1,3,4]oxadiazol-2-yl]-chroman-5-ylamine;
6-Chloro-8-[5-(2-piperidin-1-yl-ethyl)-[1,3,4]oxadiazol-2-yl]-chroman-5-ylamine;
4-[5-(5-Amino-6-chloro-chroman-8-yl)-[1,3,4]oxadiazol-2-yl]-[1,4]bipiperidinyl-1'-carboxylic acid ethyl ester;
6-Chloro-8-[5-(3-piperidin-1-yl-propyl)-[1,3,4]oxadiazol-2-yl]-chroman-5-ylamine;
6-Chloro-8-[5-(1-cyclopentyl-piperidin-4-ylmethyl)-[1,3,4]oxadiazol-2-yl]-chroman-5-ylamine oxalate salt;
6-Chloro-8-[5-(3-isopropyl-3-aza-bicyclo[3.1.0]hex-6-yl)-[1,3,4]oxadiazol-2-yl]-chroman-5-ylamine oxalate salt;
6-Chloro-8-[5-(3-cyclobutylmethyl-3-aza-bicyclo[3.1.0] hex-6-yl)-[1,3,4]oxadiazol-2-yl]-chroman-5-ylamine oxalate salt;
6-Chloro-8-[5-(3-cyclopropylmethyl-3-aza-bicyclo [3.1.0]hex-6-yl)-[1,3,4]oxadiazol-2-yl]-chroman-5-ylamine;
6-Chloro-8-{5-[1-(tetrahydro-pyran-4-yl)-piperidin-4-yl]-[1,3,4]oxadiazol-2-yl}-chroman-5-ylamine oxalate salt;

6-Chloro-8-{5-[1-(tetrahydro-pyran-4-ylmethyl)-piperidin-4-yl]-[1,3,4]oxadiazol-2-yl}-chroman-5-ylamine oxalate salt;

5-Chloro-7-[5-(1-cyclopropyl-piperidin-4-yl)-[1,3,4]oxadiazol-2-yl]-2,3-dihydro-benzofuran-4-ylamine oxalate salt;

5-Chloro-7-[5-(1-cyclobutyl-piperidin-4-yl)-[1,3,4]oxadiazol-2-yl]-2,3-dihydro-benzofuran-4-ylamine oxalate salt;

6-Chloro-8-[5-(1-cyclopropyl-piperidin-4-yl)-[1,3,4]oxadiazol-2-yl]-2,3-dihydro-benzo[1,4]dioxin-5-ylamine oxalate salt;

6-Chloro-8-{5-[1-(tetrahydro-pyran-4-yl)-piperidin-4-yl]-[1,3,4]oxadiazol-2-yl}-2,3-dihydro-benzo[1,4]dioxin-5-ylamine oxalate salt;

6-Chloro-8-{5-[1-(3-methoxy-propyl)-piperidin-4-yl]-[1,3,4]oxadiazol-2-yl}-2,3-dihydro-benzo[1,4]dioxin-5-ylamine oxalate salt;

6-Chloro-8-{5-[1-(tetrahydro-pyran-4-ylmethyl)-piperidin-4-yl]-[1,3,4]oxadiazol-2-yl}-2,3-dihydro-benzo[1,4]dioxin-5-ylamine oxalate salt;

5-Chloro-7-{5-[1-(tetrahydro-pyran-4-ylmethyl)-piperidin-4-yl]-[1,3,4]oxadiazol-2-yl}-2,3-dihydro-benzofuran-4-ylamine oxalate;

4-[5-(4-Amino-5-chloro-2,3-dihydro-benzofuran-7-yl)-[1,3,4]oxadiazol-2-yl]-[1,4]bipiperidinyl-1'-carboxylic acid ethyl ester oxalate;

3-[5-(1-Cyclobutylmethyl-piperidin-4-yl)-[1,3,4]oxadiazol-2-yl]-1-isopropyl-1H-indazole;

1-Isopropyl-3-{5-[1-(2-methoxy-ethyl)-piperidin-4-yl]-[1,3,4]oxadiazol-2-yl}-1H-indazole;

3-[5-(1-Cyclobutyl-piperidin-4-yl)-[1,3,4]oxadiazol-2-yl]-1-isopropyl-1H-indazole;

1-Isopropyl-3-[5-(1-isopropyl-piperidin-4-yl)-[1,3,4]oxadiazol-2-yl]-1H-indazole;

3-[5-(1-Cyclopropylmethyl-piperidin-4-yl)-[1,3,4]oxadiazol-2-yl]-1-isopropyl-1H-indazole;

1-Isopropyl-3-{5-[1-(3-methyl-butyl)-piperidin-4-yl]-[1,3,4]oxadiazol-2-yl}-1H-indazole;

3-[5-(1-Cyclopropyl-piperidin-4-yl)-[1,3,4]oxadiazol-2-yl]-1-isopropyl-1H-indazole;

3-[5-(1-Cyclopentyl-piperidin-4-yl)-[1,3,4]oxadiazol-2-yl]-1-isopropyl-1H-indazole;

1-Isopropyl-3-{5-[3-(3-methoxy-propyl)-3-aza-bicyclo[3.1.0]hex-6-yl]-[1,3,4]oxadiazol-2-yl}-1H-indazole oxalate salt;

3-[5-(3-Cyclobutyl-3-aza-bicyclo[3.1.0]hex-6-yl)-[1,3,4]oxadiazol-2-yl]-1-isopropyl-1H-indazole oxalate salt;

3-[5-(3-Cyclobutylmethyl-3-aza-bicyclo[3.1.0]hex-6-yl)-[ 1,3,4]oxadiazol-2-yl]-1-isopropyl-1H-indazole oxalate salt;

3-[5-(3-Cyclopropylmethyl-3-aza-bicyclo[3.1.0]hex-6-yl)-[ 1,3,4]oxadiazol-2-yl]-1-isopropyl-1H-indazole oxalate salt;

1-Isopropyl-3-{5-[1-(tetrahydro-pyran-4-ylmethyl)-piperidin-4-yl]-[1,3,4]oxadiazol-2-yl}-1H-indazole oxalate salt;

1-Isopropyl-3-{5-[1-(tetrahydro-pyran-4-yl)-piperidin-4-yl]-[1,3,4]oxadiazol-2-yl}-1H-indazole oxalate salt;

1-Isopropyl-3-[5-(2-piperidin-1-yl-ethyl)-[1,3,4]oxadiazol-2-yl]-1H-indazole oxalate salt; and 3-[5-(1-cyclobutyl piperidin-4-yl methyl)-[1,3,4]oxadiazol-2-yl]-1-isopropyl-1H-indazole oxalate salt, or their pharmaceutically acceptable salts.

3. The process for preparation of a compound of formula (I) as claimed in claim 1, which comprises:

(a) coupling the compound of formula (1) with compound of formula (2)

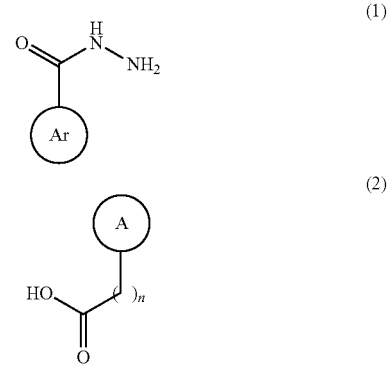

in presence of dehydrating agent to form a compound of formula (I), wherein all substitutions are as defined in claim 1, (b) optionally converting the compound of formula (I) to a pharmaceutically acceptable salt.

4. The process for preparation of a compound of formula (I) as claimed in claim 1, which comprises:

(a) coupling the compound of formula (1) with compound of formula (2)

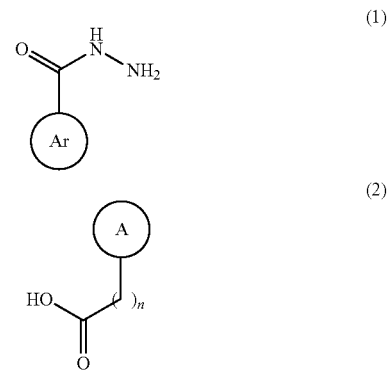

in presence of suitable solvent to form a compound of formula (4),

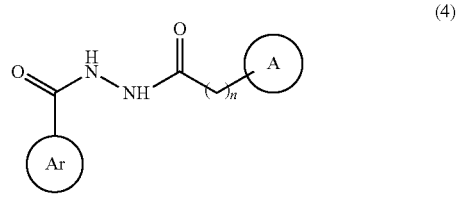

(b) cyclizing the compound of formula (4) to form a compound of formula (I), wherein all substitutions are as defined in claim 1, (c) optionally converting the compound of formula (I) to a pharmaceutically acceptable salt.

5. A pharmaceutical composition comprising a compound according to claim 1 and pharmaceutically acceptable excipients.

6. The pharmaceutical composition as claimed in claim 5, for stimulating 5 HT₄ receptors in the treatment of clinical conditions selected from the group consisting of attention deficit hyperactivity disorder, Alzheimer's disease, cognitive disorders, dementia and schizophrenia.

7. The compound as claimed in claim 1, which is selected from the group consisting of:
- 6-Chloro-8-[5-(1-cyclopropyl-piperidin-4-yl)-[1,3,4]oxadiazol-2-yl]-chroman-5-ylamine hemi fumarate;
- 6-Chloro-8-[5-(1-cyclobutyl piperdin-4-ylmethyl)-[1,3,4] oxadiazol-2-yl]-chroman-5-yl amine L(+)-tartarate salt;
- 6-Chloro-8-[5-(1-cyclobutyl piperdin-4-yl methyl)-[1,3,4] oxadiazol-2-yl]-chroman-5-yl amine;
- 1-Isopropyl-3-{5-[1-(3-methoxy propyl)piperidin-4-yl]-[1,3,4]oxadiazol-2-yl}-1H-indazole oxalate salt;
- 3-[5-(1-Cyclobutyl-piperidin-4-yl methyl)-[1,3,4]oxadiazol-2-yl]-1-isopropyl-1H-indazole L(+)-tartarate salt;
- 6-Chloro-8-[5-(3-cyclobutyl-3-aza bicyclo[3.1.0]hex-6-yl)-[1,3,4]oxadiazol-2-yl]chroman-5-ylamine oxalate salt;
- 6-Chloro-8-{5-[1-(2-methoxy-ethyl)-piperidin-4-yl]-[1,3,4]oxadiazol-2-yl}-chroman-5-ylamine;
- 6-Chloro-8-{5-[1-(3-methyl-butyl)-piperidin-4-yl]-[1,3,4]oxadiazol-2-yl}-chroman-5-ylamine;
- 6-Chloro-8-[5-(1-cyclobutylmethyl-piperidin-4-yl)-[1,3,4]oxadiazol-2-yl]-chroman-5-ylamine;
- 6-Chloro-8-[5-(1-cyclopropylmethyl-piperidin-4-yl)-[1,3,4]oxadiazol-2-yl]-chroman-5-ylamine;
- 6-Chloro-8-[5-(1-isopropyl-piperidin-4-yl)-[1,3,4]oxadiazol-2-yl]-chroman-5-ylamine;
- 6-Chloro-8-{5-[1-(3-methoxy-propyl)-piperidin-4-yl]-[1,3,4]oxadiazol-2-yl}-chroman-5-ylamine;
- 6-Chloro-8-[5-(1-cyclobutyl-piperidin-4-yl)-[1,3,4]oxadiazol-2-yl]-chroman-5-ylamine;
- 6-Chloro-8-[5-(1-cyclopentyl-piperidin-4-yl)-[1,3,4]oxadiazol-2-yl]-chroman-5-ylamine;
- 6-Chloro-8-[5-(2-piperidin-1-yl-ethyl)-[1,3,4]oxadiazol-2-yl]-chroman-5-ylamine;
- 4-[5-(5-Amino-6-chloro-chroman-8-yl)-[1,3,4]oxadiazol-2-yl]-[1,4]bipiperidinyl-1'-carboxylic acid ethyl ester;
- 6-Chloro-8-[5-(3-piperidin-1-yl-propyl)-[1,3,4]oxadiazol-2-yl]-chroman-5-ylamine;
- 6-Chloro-8-[5-(1-cyclopentyl-piperidin-4-ylmethyl)-[1,3,4]oxadiazol-2-yl]-chroman-5-ylamine oxalate salt;
- 6-Chloro-8-[5-(3-isopropyl-3-aza-bicyclo[3.1.0]hex-6-yl)-[1,3,4]oxadiazol-2-yl]-chroman-5-ylamine oxalate salt;
- 6-Chloro-8-[5-(3-cyclobutylmethyl-3-aza-bicyclo[3.1.0]hex-6-yl)-[1,3,4]oxadiazol-2-yl]-chroman-5-ylamine oxalate salt;
- 6-Chloro-8-[5-(3-cyclopropylmethyl-3-aza-bicyclo[3.1.0]hex-6-yl)-[1,3,4]oxadiazol-2-yl]-chroman-5-ylamine;
- 6-Chloro-8-{5-[1-(tetrahydro-pyran-4-yl)-piperidin-4-yl]-[1,3,4]oxadiazol-2-yl}-chroman-5-ylamine oxalate salt;
- 6-Chloro-8-{5-[1-(tetrahydro-pyran-4-ylmethyl)-piperidin-4-yl]-[1,3,4]oxadiazol-2-yl}-chroman-5-ylamine oxalate salt;
- 3-[5-(1-Cyclobutylmethyl-piperidin-4-yl)-[1,3,4]oxadiazol-2-yl]-1-isopropyl-1H-indazole;
- 1-Isopropyl-3-{5-[1-(2-methoxy-ethyl)-piperidin-4-yl]-[1,3,4]oxadiazol-2-yl}-1H-indazole;
- 3-[5-(1-Cyclobutyl-piperidin-4-yl)-[1,3,4]oxadiazol-2-yl]-1-isopropyl-1H-indazole;
- 1-Isopropyl-3-[5-(1-isopropyl-piperidin-4-yl)-[1,3,4]oxadiazol-2-yl]-1H-indazole;
- 3-[5-(1-Cyclopropylmethyl-piperidin-4-yl)-[1,3,4]oxadiazol-2-yl]-1-isopropyl-1H-indazole;
- 1-Isopropyl-3-{5-[1-(3-methyl-butyl)-piperidin-4-yl]-[1,3,4]oxadiazol-2-yl}-1H-indazole;
- 3-[5-(1-Cyclopropyl-piperidin-4-yl)-[1,3,4]oxadiazol-2-yl]-1-isopropyl-1H-indazole;
- 3-[5-(1-Cyclopentyl-piperidin-4-yl)-[1,3,4]oxadiazol-2-yl]-1-isopropyl-1H-indazole;
- 1-Isopropyl-3-{5-[3-(3-methoxy-propyl)-3-aza-bicyclo[3.1.0]hex-6-yl]-[1,3,4]oxadiazol-2-yl}-1H-indazole oxalate salt;
- 3-[5-(3-Cyclobutyl-3-aza-bicyclo[3.1.0]hex-6-yl)-[1,3,4]oxadiazol-2-yl]-1-isopropyl-1H-indazole oxalate salt;
- 3-[5-(3-Cyclobutylmethyl-3-aza-bicyclo[3.1.0]hex-6-yl)-[1,3,4]oxadiazol-2-yl]-1-isopropyl-1H-indazole oxalate salt;
- 3-[5-(3-Cyclopropylmethyl-3-aza-bicyclo[3.1.0]hex-6-yl)-[1,3,4]oxadiazol-2-yl]-1-isopropyl-1H-indazole oxalate salt;
- 1-Isopropyl-3-{5-[1-(tetrahydro-pyran-4-ylmethyl)-piperidin-4-yl]-[1,3,4]oxadiazol-2-yl}-1H-indazole oxalate salt;
- 1-Isopropyl-3-{5-[1-(tetrahydro-pyran-4-yl)-piperidin-4-yl]-[1,3,4]oxadiazol-2-yl}-1H-indazole oxalate salt;
- 1-Isopropyl-3-[5-(2-piperidin-1-yl-ethyl)-[1,3,4]oxadiazol-2-yl]-1H-indazole oxalate salt and
- 3-[5-(1-cyclobutyl piperidin-4-yl methyl)-[1,3,4]oxadiazol-2-yl]-1-isopropyl-1H-indazole oxalate salt.

8. The compound as claimed in claim 1, which is selected from the group consisting of:
- 6-Chloro-8-[5-(1-cyclopropyl-piperidin-4-yl)-[1,3,4]oxadiazol-2-yl]-chroman-5-ylamine;
- 6-Chloro-8-[5-(1-cyclopropyl-piperidin-4-yl)-[1,3,4]oxadiazol-2-yl]-chroman-5-ylamine hemi fumarate;
- 6-Chloro-8-[5-(1-cyclobutyl piperdin-4-ylmethyl)-[1,3,4] oxadiazol-2-yl]-chroman-5-yl amine;
- 3-[5-(1-Cyclobutyl-piperidin-4-yl methyl)-[1,3,4]oxadiazol-2-yl]-1-isopropyl-1H-indazole L(+)-tartarate salt;
- 1-Isopropyl-3-{5-[1-(3-methoxy propyl)piperidin-4-yl]-[1,3,4]oxadiazol-2-yl}-1H-indazole;
- 1-Isopropyl-3-{5-[1-(3-methoxy propyl)piperidin-4-yl]-[1,3,4]oxadiazol-2-yl}-1H-indazole oxalate salt;
- 6-Chloro-8-{5-[1-(tetrahydro-pyran-4-ylmethyl)-piperidin-4-yl]-[1,3,4]oxadiazol-2-yl}-chroman-5-ylamine; and
- 6-Chloro-8-{5-[1-(tetrahydro-pyran-4-ylmethyl)-piperidin-4-yl]-[1,3,4]oxadiazol-2-yl}-chroman-5-ylamine oxalate salt.

9. The compound as claimed in claim 1, which is selected from the group consisting of:
- 6-Chloro-8-[5-(1-cyclopropyl-piperidin-4-yl)-[1,3,4]oxadiazol-2-yl]-chroman-5-ylamine;
- 1-isopropyl-3-{5-[1-(3-methoxy propyl)piperidin-4-yl]-[1,3,4]oxadiazol-2-yl}-1H-indazole;
- 3-[5-(1-cyclobutyl-piperidin-4-yl methyl)-[1,3,4]oxadiazol-2-yl]-1-isopropyl-1H-indazole;
- 6-chloro-8-[5-(3-cyclobutyl-3-aza bicyclo[3.1.0]hex-6-yl)-[1,3,4]oxadiazol-2-yl]chroman-5-yl amine;
- 4-[5-(8-Amino-7-chloro-2,3-dihydro benzo[1,4]dioxan-5-yl)-[1,3,4]oxadiazol-2-yl]-[1,4]bipiperidinyl-1'-carboxylic acid ethyl ester;
- 5-Chloro-7-{5-[1-(tetrahydro pyran-4-yl) piperidin-4-yl]-[1,3,4]oxadiazol-2-yl}-2,3-dihydro benzofuran-4-yl amine;
- 6-Chloro-8-[5-(1-cyclopentyl-piperidin-4-ylmethyl)-[1,3,4]oxadiazol-2-yl]-chroman-5-ylamine;

6-Chloro-8-[5-(3-isopropyl-3-aza-bicyclo[3.1.0]hex-6-yl)-[1,3,4]oxadiazol-2-yl]-chroman-5-ylamine;
6-Chloro-8-[5-(3-cyclobutylmethyl-3-aza-bicyclo[3.1.0]hex-6-yl)-[1,3,4]oxadiazol-2-yl]-chroman-5-ylamine;
6-Chloro-8-{5-[1-(tetrahydro-pyran-4-yl)-piperidin-4-yl]-[1,3,4]oxadiazol-2-yl}-chroman-5-ylamine;
6-Chloro-8-{5-[1-(tetrahydro-pyran-4-ylmethyl)-piperidin-4-yl]-[1,3,4]oxadiazol-2-yl}-chroman-5-ylamine;
5-Chloro-7-[5-(1-cyclopropyl-piperidin-4-yl)-[1,3,4]oxadiazol-2-yl]-2,3-dihydro-benzofuran-4-ylamine;
5-Chloro-7-[5-(1-cyclobutyl-piperidin-4-yl)-[1,3,4]oxadiazol-2-yl]-2,3-dihydro-benzofuran-4-ylamine;
6-Chloro-8-[5-(1-cyclopropyl-piperidin-4-yl)-[1,3,4]oxadiazol-2-yl]-2,3-dihydro-benzo[1,4]dioxin-5-ylamine;
6-Chloro-8-{5-[1-(tetrahydro-pyran-4-yl)-piperidin-4-yl]-[1,3,4]oxadiazol-2-yl}-2,3-dihydro-benzo[1,4]dioxin-5-ylamine;
6-Chloro-8-{5-[1-(3-methoxy-propyl)-piperidin-4-yl]-[1,3,4]oxadiazol-2-yl}-2,3-dihydro-benzo[1,4]dioxin-5-ylamine;
6-Chloro-8-{5-[1-(tetrahydro-pyran-4-ylmethyl)-piperidin-4-yl]-[1,3,4]oxadiazol-2-yl}-2,3-dihydro-benzo[1,4]dioxin-5-ylamine;
5-Chloro-7-{5-[1-(tetrahydro-pyran-4-ylmethyl)-piperidin-4-yl]-[1,3,4]oxadiazol-2-yl}-2,3-dihydro-benzofuran-4-ylamine;
4-[5-(4-Amino-5-chloro-2,3-dihydro-benzofuran-7-yl)-[1,3,4]oxadiazol-2-yl]-[1,4]bipiperidinyl-1'-carboxylic acid ethyl ester;
1-Isopropyl-3-{5-[3-(3-methoxy-propyl)-3-aza-bicyclo[3.1.0]hex-6-yl]-[1,3,4]oxadiazol-2-yl}-1H-indazole;
3-[5-(3-Cyclobutyl-3-aza-bicyclo[3.1.0]hex-6-yl)-[1,3,4]oxadiazol-2-yl]-1-isopropyl-1H-indazole;
3-[5-(3-Cyclobutylmethyl-3-aza-bicyclo[3.1.0]hex-6-yl)-[1,3,4]oxadiazol-2-yl]-1-isopropyl-1H-indazole;
3-[5-(3-Cyclopropylmethyl-3-aza-bicyclo[3.1.0]hex-6-yl)-[1,3,4]oxadiazol-2-yl]-1-isopropyl-1H-indazole;
1-Isopropyl-3-{5-[1-(tetrahydro-pyran-4-ylmethyl)-piperidin-4-yl]-[1,3,4]oxadiazol-2-yl}-1H-indazole;
1-Isopropyl-3-{5-[1-(tetrahydro-pyran-4-yl)-piperidin-4-yl]-[1,3,4]oxadiazol-2-yl}-1H-indazole; and
1-Isopropyl-3-[5-(2-piperidin-1-yl-ethyl)-[1,3,4]oxadiazol-2-yl]-1H-indazole, and their pharmaceutically acceptable salts.

10. A pharmaceutical composition comprising a compound according to claim 8 and pharmaceutically acceptable excipients.

11. The compound of claim 2, wherein said compound is 6-Chloro-8-[5-(1-cyclopropyl-piperidin-4-yl)-[1,3,4]oxadiazol-2-yl]-chroman-5-ylamine hemi fumarate.

12. The compound of claim 2, wherein said compound is 6-Chloro-8-[5-(1-cyclobutyl piperidin-4-ylmethyl)-[1,3,4]oxadiazol-2-yl]-chroman-5-yl amine L(+)-tartarate salt.

13. The compound of claim 2, wherein said compound is 1-Isopropyl-3-{5-[1-(3-methoxy-propyl)-piperidin-4-yl]-[1,3,4]oxadiazol-2-yl}-1H-indazole oxalate salt.

14. The compound of claim 2, wherein said compound is 6-Chloro-8-{5-[1-(tetrahydro-pyran-4-ylmethyl)-piperidin-4-yl]-[1,3,4]oxadiazol-2-yl}-chroman-5-ylamine oxalate salt.

* * * * *